(12) United States Patent
Hankemeier et al.

(10) Patent No.: US 9,625,427 B2
(45) Date of Patent: Apr. 18, 2017

(54) METHOD AND DEVICE FOR SOLVENT EVAPORATION FROM A LIQUID FEED

(71) Applicant: UNIVERSITEIT LEIDEN, Leiden (NL)

(72) Inventors: Thomas Hankemeier, Leiden (NL); Jan-Willem Schoonen, Leiden (NL); Heiko Jan Van Der Linden, Leiden (NL); Paul Vulto, Leiden (NL)

(73) Assignee: UNIVERSITEIT LEIDEN, Leiden (NL)

( * ) Notice: Subject to any disclaimer, the term of this patent is extended or adjusted under 35 U.S.C. 154(b) by 218 days.

(21) Appl. No.: 14/384,943

(22) PCT Filed: Mar. 12, 2013

(86) PCT No.: PCT/NL2013/050163
§ 371 (c)(1),
(2) Date: Sep. 12, 2014

(87) PCT Pub. No.: WO2013/137726
PCT Pub. Date: Sep. 19, 2013

(65) Prior Publication Data
US 2015/0075300 A1 Mar. 19, 2015

(30) Foreign Application Priority Data

Mar. 13, 2012 (NL) .................................. 2008483
Mar. 13, 2012 (NL) .................................. 2008484

(51) Int. Cl.
*G01N 1/22* (2006.01)
*G01N 30/12* (2006.01)
(Continued)

(52) U.S. Cl.
CPC .............. *G01N 30/12* (2013.01); *B01D 1/00* (2013.01); *G01N 1/4022* (2013.01);
(Continued)

(58) Field of Classification Search
CPC ....................................................... G01N 1/22
(Continued)

(56) References Cited

U.S. PATENT DOCUMENTS 3,127,300 A * 3/1964 Maggio .................... B01D 1/00
159/32
4,079,585 A * 3/1978 Helleur .................... B01D 1/14
159/47.3
(Continued)

FOREIGN PATENT DOCUMENTS

| CN | 101545889 A | 9/2009 |
|---|---|---|
| WO | 9962607 | 12/1999 |
| WO | 2010112699 A1 | 10/2010 |

OTHER PUBLICATIONS

Written Opinion of the International Searching Authority, PCT/NL2013/050163, Dec. 3, 2013.*
(Continued)

*Primary Examiner* — Clayton E Laballe
*Assistant Examiner* — Kevin Butler
(74) *Attorney, Agent, or Firm* — Nixon Peabody LLP

(57) ABSTRACT

The present invention relates to a device and an arrangement for selective solvent evaporation from a liquid feed, the feed comprising one or more components diluted in at least a first solvent or a solvent blend, comprising: a) a first tubular vessel having a distal end or a channel suitable for the formation of a droplet of a first volume, at an inflow rate n, at the tip or in the lumen of the tubular vessel, and b) means for subjecting the droplet to a solvent removal step at an evaporation rate $r_2$ to evaporate at least part of the first solvent or solvent blend, to accumulate the components in the feed in the droplet during the evaporation process at an accumulation rate $r_3$, to obtain a concentrated feed volume in a concentrated droplet, wherein the evaporation and/or inflow rates are continuously adjusted to achieve a desired
(Continued)

accumulation rate. The invention further relates to a method for selective solvent removal from an analyte mixture obtained in a chromatographic separation process.

23 Claims, 10 Drawing Sheets

(51) Int. Cl.
    *B01D 1/00*           (2006.01)
    *G01N 30/46*         (2006.01)
    *G01N 30/62*         (2006.01)
    *G01N 1/40*          (2006.01)
    *G01N 1/24*          (2006.01)
    *G01N 30/02*         (2006.01)

(52) U.S. Cl.
    CPC ........... *G01N 30/463* (2013.01); *G01N 30/62* (2013.01); *G01N 1/2214* (2013.01); *G01N 1/2273* (2013.01); *G01N 1/24* (2013.01); *G01N 1/405* (2013.01); *G01N 2001/2223* (2013.01); *G01N 2001/4027* (2013.01); *G01N 2030/027* (2013.01); *G01N 2030/126* (2013.01)

(58) Field of Classification Search
    USPC ...................................................... 73/863.21
    See application file for complete search history.

(56) References Cited

U.S. PATENT DOCUMENTS

| | | | | |
|---|---|---|---|---|
| 4,087,248 | A * | 5/1978 | Miles | B01L 9/54 422/63 |
| 4,311,668 | A * | 1/1982 | Solomon | G01N 30/06 210/198.2 |
| 4,846,935 | A * | 7/1989 | Giesselmann | A23F 5/486 202/267.1 |
| 4,958,529 | A * | 9/1990 | Vestal | G01N 30/7273 250/288 |
| 4,960,992 | A * | 10/1990 | Vestal | G01N 30/7253 250/288 |
| 5,268,303 | A | 12/1993 | Bourne et al. | |
| 5,441,878 | A * | 8/1995 | Thies | C12N 11/04 264/14 |
| 5,762,877 | A * | 6/1998 | Brewer | G01N 1/40 210/198.3 |
| 6,461,572 | B1 * | 10/2002 | Calfee | B01D 3/00 159/43.1 |
| 6,620,620 | B1 * | 9/2003 | Anderson | B01D 1/0082 159/44 |
| 2002/0045270 | A1 | 4/2002 | Schurenberg et al. | |
| 2003/0148538 | A1 | 8/2003 | Ng | |
| 2003/0168392 | A1 | 9/2003 | Masuda et al. | |
| 2004/0203175 | A1 * | 10/2004 | Li | G01N 1/40 436/180 |
| 2006/0110833 | A1 | 5/2006 | Agnes et al. | |
| 2008/0241956 | A1 | 10/2008 | Hirai et al. | |
| 2010/0092683 | A1 | 4/2010 | Ermantraut et al. | |
| 2015/0075300 | A1 * | 3/2015 | Hankemeier | G01N 30/12 73/863.21 |

OTHER PUBLICATIONS

Reichenbach et al., "Quantification in Comoprehensive Two-Dimensional Liquid Chromatography", Anal. Chem., 2009, 81, 5099-5101.*
Vivo-Truyols et al., "Probability of failure of the watershed algorithm for peak detection in comprehensive two-dimensional chromatography", Journal of Chomatography A., 1217(8):1375-1385 (2010).*
Matthiessen et al., "Use of a Keeper to Enhance the Recovery of Volatiole Polycyclic Aromatic Hydrocarbons in HPLC Analysis", Chromaltographia, 45(1):190-194 (1997).*
Moret et al., "On-Line Solvent Evaporator for Coupled LC Systems: Further Developments", J. High Resol. Chromatogr., 19(8) 434-438 (1996).*
Moret et al., "On-line high-performance liquid chromatography-solvent evaporation-high-performance liquid chromatography-capillary gas chromatography-flame ionisation detection for the analysis of mineral oil polyaromatic hydrocarbons in fatty foods", Journal of Chromatography A, 750(1-2):361-368 (1996).*
Tian et al., "MUltidimensional liquid chromatography system wih an innovative solvent evaporation interface", Journal of CHromatography A, 1137(a):42-48 (2006).*
Moret et al., "Mineral oil polyaromatic hydrocarbons in foods, e.g. from jute bags, by on-line LC-solvent evaporation (SE)-LC-GC-FID", Z Lebensm Unfers Forsch A, 204(3):241-246 (1997).*
Shin et al., "Machine vision for digital microfluidics", Reviwe of Scientific Instruments, 81(1):014302-1 (2010).*
Suslick, "Sonochemistry" "Kirk-Othmer Encyclopedia of Chemical Technology", John Wiley & Sons, Inc 4th vol. 26: New York, 1998, pp. 516-541.*
Alexander et al., "Comprehensive two-dimensional liquid chromatography separations of pharmaceutical samples using dual Fused-Core columns in the 2nd dimension", Journal of Chromatography A, 1216(9):1338-1345 (2009).*
Roy et al., "Development of Comprehensive Two-Dimensional High Temperature Liquid Chromatography x Gel Permeation Chromatography for Characterization of Polyolefins", Macromolecules, 43(8):3710-3720 (2010).*
Tian et al., "Comprehensive two-dimesional liquid chromatography (NPLCxRPLE) with vacuum-evaporation interface", J. Sep. Sci., 31(10):1677-1685 (2008).*
Fairchild et al., "Approaches to comprehensive multidimensional liquid chromatography systems", Journal of Chromatography A, 1216(9):1363-1371 (2009).*
Walker et al., "An evaporaton-based microfluidic sample concentration method", Lab Chip, 2(2):57-61 (2002).*
Ding et al., "A vacuum assisted dynamic evaporation interface for two-dimensional normal phase/revere phase liquid chromatography", Journal of Chomatography A, 1217(34):5477-5483 (2010).*
Bedani et al., "Optimal gradient operation in comprehensive liquid chromatography x liquid chromatography systems with limited orthogonality", Analytica Chimica Acta, 654(1):77-84 (2009).
Bobeldijk et al., "High-performance liquid chromatography—ToxPrint: chromatographic analysis with a novel (geno) toxicity detection", Journal of Chromatography A, 918(2):277-291 (2001).
Ding et al., "A vacuum assisted dynamic evaporation interface for two-dimensional normal phase/reverse phase liquid chromatography", Journal of Chromatography A, 1217(34):5477-5483 (2010).
Dugo et al., "Comprehensive two-dimensional liquid chromatography to quantify polyphenols in red wines", Journal of chromatography A, 1216(44):7483-7487 (2009).
Dutriez et al., "Advances in Quantitative Analysis of Heavy Petroleum Fractions by Liquid Chromatography-High-Temperature Comprehensive Two-Dimensional Gas Chromatography: Breakthrough for Conversion Processes", Energy Fuels, 24:4430-4438 (2010).
Eeltink et al., "Selection of Column Dimensions and Gradient Conditions to Maximize the Peak-Production Rate in comprehensive Off-Line Two-Dimensional Liquid Chromatography Using Monolithic Columns", Anal. Chem., 82(16):7015-7020 (2010).
Francois et al., "Comprehensive liquid chromatography: Fundamental aspects and practical considerations—A review", Analytica Chimica Acta, 641(1-2):14-31 (2009).
Francois et al., "Considerations on comprehensive and off-line supercritical fluid chromatography x reversed-phase iquid chromatography for the analysis of triacylglycerols in fish oil", J. Sep. Sci., 33(10):1504-1512 (2010).
Magni et al., "Concurrent solvent recondensation large sample volume splitless injection", J. Sep. Sci.,, 26(17):1491-1498 (2003).

(56) References Cited

OTHER PUBLICATIONS

Matthiessen et al., "Use of a Keeper to Enhance the Recovery of Volatile Polycyclic Aromatic Hydrocarbons in HPLC Analysis", Chromatographia, 45(1):190-194 (1997).

Moret et al., "Mineral oil polyaromatic hydrocarbons in foods, e.g. from jute bags, by on-line LC-solvent evaporation (SE-LC-GC-FID", Z Lebensm Unters Forsch A, 204(3):241-246 (1997).

Moret et al., "On-line high-performance liquid chromatography-solvent evaporation-high-performance liquid chromatography-capillary gas chromatography-flame ionisation detection for the analysis of mineral oil polyaromatic lydrocarbons in fatty foods", Journal of Chromatography A, 750(1-2):361-368 (1996).

Moret et al., "On-Line Solvent Evaporator for Coupled LC Systems: Further Developments", J. High Resol. Chromatogr., 19(8):434-438 (1996).

Moret et al., "On-line Solvent Evaporator for Coupled Normal Phase-Reversed Phase High-Performance Liquid Chromatography Systems: Heavy Polycyclic Aromatic Hydrocarbons Analysis", J. Microcolumn Separations, 13 (1):13-18 (2001).

Potts et al., "The impact of sampling time on peak capacity and analysis speed in on-line comprehensive two-dimensional liquid chromatography", Journal of Chromatography A, 1217(36):5700-5709 (2010).

Reichenbach et al., "Quantification in Comprehensive Two-Dimensional Liquid Chromatography", Anal. Chem., 81 (12):5099-5101 (2009).

Reichenbach et al., "Smart Templates for Peak Pattern Matching with Comprehensive Two-Dimensional Liquid Chromatography", Journal of Chromatography, 1216(16):3458-3466 (2009).

Shin et al., "Machine vision for digital microfluidics", Review of Scientific Instruments, 81(1):014302-1 (2010).

Tian et al., "Comprehensive two-dimensional liquid chromatography (NPLCxRPLC) with vacuum-evaporation interface", J. Sep. Sci., 31(10):1677-1685 (2008).

Tian et al., "Multidimensional liquid chromatography system with an innovative solvent evaporation interface", Journal of Chromatography A, 1137(1):42-48 (2006).

Vivo-Truyols et al., "Comprehensive Study on the Optimization of Online Two-Dimensional Liquid Chromatographic Systems Considering Losses in Theoretical Peak Capacity in First- and Second-Dimensions: A Pareto-Optimality Approach", Anal. Chem., 82(20):8525-8536 (2010).

Vivo-Truyols et al., "Probability of failure of the watershed algorithm for peak detection in comprehensive two-dimensional chromatography", Journal of Chromatography A, 1217(8):1375-1385 (2010).

Walker et al., "An evaporation-based microfluidic sample concentration method", Lab Chip, 2(2):57-61 (2002).

Wei et al., "A comprehensive two-dimensional normal-phase x reversed-phase liquid chromatography based on the modification of mobile phases", Journal of Chromatography A, 1216(44):7466-7471 (2009).

* cited by examiner

METHOD AND DEVICE FOR SOLVENT EVAPORATION FROM A LIQUID FEED

CROSS REFERENCE TO RELATED APPLICATIONS

This application is a 35 U.S.C. §371 National Phase Entry Application of International Application No. PCT/NL2013/050163 filed Mar. 12, 2013, which designates the U.S., and which claims benefit under 35 U.S.C. 119(d) of Application No. 2008483 (NL) filed Mar. 13, 2012 and Application No. 2008484 (NL) filed Mar. 13, 2012, the contents of both of which are incorporated herein by reference in their entirety.

FIELD OF THE INVENTION

The subject invention relates to a method and a device for the processing of analytical samples and selective solvent removal from liquid analytical samples in (bio)chemical analysis.

The subject invention may advantageously be used to improve the resolution of multi-dimensional chromatographic separations, to avoid solvent interference in NMR and electrospray-MS and to improve biochemical assays like, among others, enzyme assays.

The subject invention lends itself particularly well for low sample flow rates and small sample volumes.

Furthermore, the invention can be used to remove solvents from a sample or sample stream where solvents may interfere in a subsequent step. Such interferences include the presence of protonated eluents in NMR detection or the presence of non-aqueous solvents which have negative influences in bio-assays (i.e. protein denaturation). The method is particularly suitable for very small liquid flow rates commonly less than 5 m L/minute.

Solvent removal is an important unit operation in analytical chemistry. For instance in multi-dimensional liquid chromatography the removal of the first dimension's eluent avoids miscibility problems occurring when introducing sample amounts coming from the first dimension into the second separation dimension. In case the first dimension is based on a normal-phase solid phase the eluent will commonly be hydrophobic in nature and often not miscible with the polar (e.g. aqueous) eluent used in the second dimension. This commonly limits the use of multi-dimensional liquid chromatography and a solution for this issue is desired as the need for liquid chromatography methods for the separation of the very complex samples (e.g. from application in metabolomics, proteomics) is increasing.

Comprehensive two-dimensional liquid chromatography, often abbreviated 2DLC, MDLC or LCxLC, the latter being referred to herein, is an important analytical tool for analyzing complex samples that cannot easily be subjected to gas chromatographic separation. In this technique, two chromatographic separation columns with orthogonal separation behaviour, i.e. employing columns that have a different separation mechanism or characteristics, so that sample bands that are poorly resolved on the first column may be separated on the second column, are linked sequentially, thereby having theoretically a separation power close to the product of the peak resolving power of both columns.

An example of an LCxLC application is the separation of protein mixtures by ion exchange chromatography followed by reverse-phase LC. These separation methods are considered orthogonal, whereby the first separation is based on charge separation through salt elution, while the second separation is based on hydrophobicity using gradient elution with organic solvents. The solvents employed in this method tend to be incompatible with each other.

The theoretically calculated resolving power of LCxLC and related multidimensional separation techniques involving at least one liquid chromatography step, followed by a further analytical or separation technique that requires a different solvent has not been achieved in practice yet. This is at least in part due to difficulties with the necessary solvent exchange at the interface between the two methods. In particular, problems arise due to the incompatibility of solvents between the first and second dimension, e.g. a strong eluent on a primary column becomes a weak eluent on the secondary column which ultimately deteriorates the separation performance.

In order to achieve the maximum chromatographic performance in both types of columns, the eluent type must therefore be changed prior to entry of a sample or sample fraction from the first column, which may lead to sample dilution. Sample dilution negatively affects detectability, solubility and leads to loss of analytes and/or solvents leading to various chromatographic errors, peak band dispersions negatively affecting the peak bandwidth injected on the second column, thereby reducing the chromatographic separation performance.

US-A-2003/0168392 discloses an approach to remove the first separation solvent. Herein, samples are trapped after the first separation onto individual intermediate trapping columns. However, this procedure leads to loss of analyte due to adherence to the column material, which is particularly undesired for small samples.

In Tian, H., et al., J Chromatogr A, 2006. 1137(1): p. 42-8, and Tian, H., J. Xu, and Y. Guan, J Sep Sci, 2008. 31(10): p. 1677-85, an LCxLC technique is disclosed in which evaporation of the solvent from a sample collected from a primary column takes place within a capillary, using reduced pressure to enable an evaporation interface. A disadvantage of the described technique is that the large surface-to-volume ratio inside the capillary results in significant analyte adsorption to the capillary wall and sample volumes transferred to the second dimension are typically a magnitude higher, resulting in deteriorated sample-eluent miscibility. Another disadvantage is that evaporated gas cannot be easily removed from the capillary, as result of which a direct injection into the next column will be difficult.

US-A-2004/203175 discloses an apparatus and a method for concentrating and collecting analytes from a flowing liquid stream. This is performed by an apparatus for concentrating and collecting one or more analytes in a flowing liquid stream of a carrier solvent composed of one or more solvent components. The apparatus includes a transfer tube which forms one or more aligned bores, each having an inlet and an outlet, the inlet being adapted to accept the flowing liquid stream, and the outlet being adapted to form continuously replaced, hanging droplets of the liquid stream. The apparatus also includes a collection device mounted below the outlet of the transfer tube for collecting the droplets. The apparatus includes a device for heating the liquid stream in the transfer tube to a temperature sufficient to cause partial evaporation of the carrier solvent from the hanging droplets but not exceeding the boiling point of the carrier solvent; and a device for heating the collection device to a temperature sufficient to cause further evaporation of the carrier solvent.

WO-A-99/62607 discloses an apparatus for forming a prescribed concentration of a substance in a mixture with a fluid from a dilute mixture which is a solution of a solute in a solvent, the apparatus including a frame carrying a vertically oriented syringe, a stepper motor, a laser micrometer, a heater for heating and evaporating a drop of the solution suspended from the syringe to concentrate. A problem with the disclosed process is that the laser micrometer depends strongly on bulk properties of droplets, which may change unexpectedly, e.g. in the case of crystallization of compounds therein, or if the composition changes its optical properties.

U.S. Pat. No. 6,620,620 discloses a drop-by-drop evaporation of a liquid or solution controlled by monitoring the disappearance of each successive droplet and by actuating the deposition of the next droplet until the desired volume is deposited. The device and process disclosed focus on the deposition of roughly identical droplets, which are subjected to evaporation when in contact with substrate. The process has the disadvantage that valuable components may be lost due to adherence to the surface.

Furthermore, both processes disclosed may lead to strongly reduced fluid volumes in the sample droplets, which may increase the reactivity of the solutes or components diluted in the solvent droplets.

In any of the above described methods, the samples may be evaporated to dryness leading to potentially severe analyte loss and/or analyte degradation. A further issue resides in the fact that since the evaporated sample volume may change during gradient runs, due to solvent composition changes, the resolution offered by quantitative LCxLC may be jeopardized.

Accordingly, there remains a need for improving the chromatographic separation power of LCxLC systems, without the issues raised above.

Similarly when an LC unit is coupled to other analytical means, such as for instance NMR, or mass spectrometry, the presence of the elution solvents may cause issues, or disturb the measurement, such as ion-suppression in mass-spectrometry.

Hence, there is a significant need for a technology that facilitates the exchange of eluent types while the aforementioned negative effects are significantly decreased or eliminated. More specifically, there remains a need for a technique that allows rapid and effective handling of small samples and easy solvent exchange without significant loss of solutes.

Accordingly, in a first aspect, the present invention relates to a device for selective solvent evaporation from a liquid feed, the feed comprising one or more components diluted in at least a first solvent or a solvent blend, comprising:

a) a first essentially tubular vessel having a distal end or a channel suitable for the formation of a droplet of a first volume, at an inflow rate $r_1$, at the tip or in the lumen of the tubular vessel or channel, and b) means for subjecting the droplet to a solvent evaporation step at an evaporation rate $r_2$ to evaporate at least part of the first solvent or solvent blend, and to accumulate the analyte components in the feed in the droplet during the evaporation process at an accumulation rate $r_3$, to obtain a concentrated feed volume in a second droplet, wherein the evaporation and/or inflow rates are continuously adjusted to achieve a desired accumulation rate, and c) means for diluting the concentrated sample droplet in a second solvent or solvent blend to obtain a re-diluted sample.

In a further aspect, the present invention relates to a device for selective solvent evaporation from a liquid feed, the feed comprising one or more components diluted in at least a first solvent or a solvent blend, comprising:

i) a first essentially tubular vessel having a distal end or a channel suitable for the formation of a droplet of a first volume, at an inflow rate $r_1$, at the tip or in the lumen of the tubular vessel or channel, and ii) means for subjecting the droplet to a solvent evaporation step at an evaporation rate $r_2$ to evaporate at least part of the first solvent or solvent blend, and to accumulate the analyte components in the feed in the droplet during the evaporation process at an accumulation rate $r_3$, to obtain a concentrated feed volume in a now concentrated or enriched droplet, wherein the evaporation and/or inflow rates are continuously adjusted to achieve a desired accumulation rate, the device further comprising an automated control system comprising a machine vision unit that sequentially acquires one or more images of the droplet, processes the acquired images to determine one or more droplet parameters; and communicates the parameters to a comparison means.

In a further aspect, the subject invention relates to an arrangement for the multi-dimensional separation of a liquid feed comprising one or more sample components, comprising:

i) at least a first separation device for the separation of components in the sample diluted in a first solvent or solvent blend in a first dimension into a first liquid feed comprising one or more components; and ii) a device according to the invention for selective solvent evaporation from the first liquid feed to obtain one or more concentrated droplets, and iii) at least a second separation device for the separation of the components in the concentrated sample droplets in a second dimension.

In yet a further aspect, the subject invention relates to a process for the selective solvent removal from a liquid feed comprising one or more components diluted in at least a first solvent or a solvent blend, comprising the steps of:

a) forming an amount of the feed derived from a first separation device into a droplet with a first defined volume at the distal end or within a tubular vessel at a defined inflow rate $r_1$ at the tip or in the lumen of the vessel, and b) subjecting the droplet to a solvent removal step to remove at least part of the solvent or solvent blend at a defined solvent evaporation rate $r_2$ to remove at least part of the first solvent or solvent blend, and accumulation of components in the sample in the droplet during the solvent removal process at a rate of the accumulation $r_3$, to obtain a concentrated sample droplet; wherein rates $r_1$ and $r_2$ depend on accumulation flow rate $r_3$.

In yet a further aspect, the subject invention also relates to the use of droplet bulk property independent control of the evaporation of a sample in droplets using machine vision.

BRIEF DESCRIPTION OF THE FIGURES

These and further features can be gathered from the claims, description and drawings and the individual features, both alone and in the form of sub-combinations, can be realized in an embodiment of the invention and in other fields and can represent advantageous, independently protectable constructions for which protection is hereby claimed. Embodiments of the invention are described in greater detail hereinafter relative to the drawings, wherein:

DETAILED DESCRIPTION OF THE INVENTION

Figure 1:
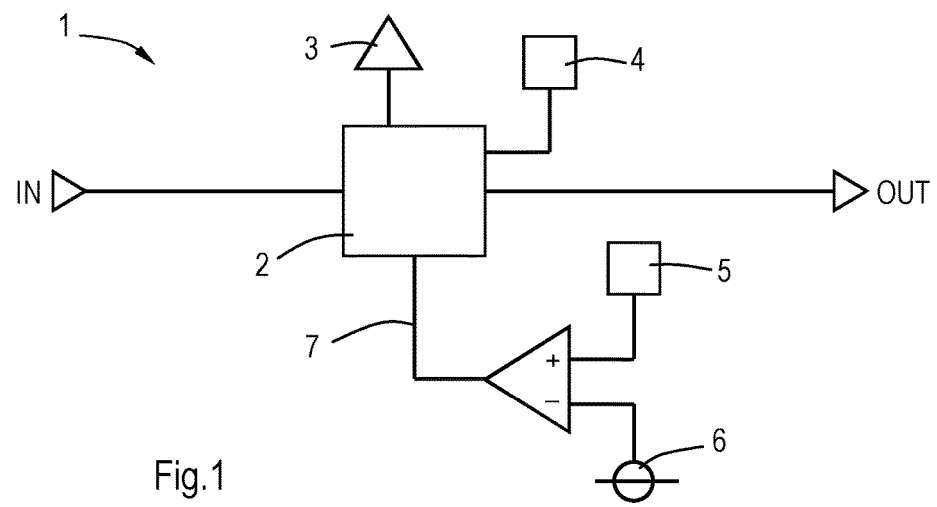
FIG. 1 discloses a schematic overview of the principle for the measurement and control of a device according to the present invention.

The present invention relates to a process, device and arrangement, all making use of selective solvent evaporation from a liquid feed.

The present invention allows to selectively remove solvent from samples derived from complex mixtures of analytes, i.e. preferably of chemical or biochemical components, in particular those that have been subjected to a separation into compounds in a first separation treatment. The sample itself may comprise a single component, or a mixture of components which may be complex.

The solvent removal is preferably performed by evaporating the solvent(s). This evaporation process can be mathematically modelled as a flow process where the flows can be mass flows (kg/s), mole flows (mole/s), volume flows (L/s) or other flows suitable to describe the process.

In the present process, $r_1$ is the rate of inflow of a sample, $r_2$ is the rate of solvent removal, preferably through evaporation, and $r_3$ is the rate of the accumulation of compounds in the liquid volume remaining in the droplet during the evaporation process. Due to the conservation of mass, the flow of compounds through the device as set out in general formula I:

$$r_1 = r_2 + r_3 \quad (I)$$

In the case that there is more than one compound present in the liquid, e.g. a dissolved species B in a solvent A, different flow balances can be formulated as in formula IIa and b:

$$r_{1,A} = r_{2,A} + r_{3,A} \quad (IIa)$$

$$r_{1,B} = r_{2,B} + r_{3,B} \quad (IIb)$$

If more compounds are present, a flow balance equation is added for each compound species.

The term "liquid feed" herein refers to a fluid under conditions of the process/separation method. The feed arrives at the tubular vessel in liquid phase, wherein preferably all components are dissolved. This may be a normally liquid solvent or solvent blend, or it may be one or more supercritical gases, e.g. liquid carbon dioxide.

The term "continuously adjusted" herein has the meaning that the droplets are continuously controlled, and adjusted if required.

The term "feed" refers to a volume or aliquot of fluid as set out above passing through the separation process prior to entry of the device, or the beginning of the process according to invention.

The liquid feed typically is a liquid aliquot of a feed comprising one or more components, typically of a complex analyte mixture. The components may be complex compounds, mixtures or salts thereof, however may also be pure chemical compounds. Typically the subject process would be ideally employed to separate a complex analyte mixture into its constituent components. The term "comprising" has the meaning of also entailing the term "consisting" within the present specification.

A droplet as described herein above refers to a meniscus, droplet sheet or a roundedly shaped droplet. The droplet is a small element of liquid, bounded almost completely by free gas/liquid surfaces with the exception of the surface boundary provided by the distal end of the tubular vessel.

The droplet is formed when liquid accumulates in the vessel in the case of a meniscus, or a pendant or standing droplet in the case of a tip of a tubular vessel or a droplet sheet in the case of for instance an elongated channel at the end of the vessel, as for instance provided by a channel etched into a microfluidic chip. If the vessel, the distal end of the vessel or the channel are pointing essentially downward, this will likely result in a pendant droplet, meniscus or droplet sheet, all of which will be referred to as "droplet" herein.

A pendant droplet is suspended from the end of a tube by surface tension. Alternatively, the droplet may be formed by pushing a liquid upward through an essentially upward pointing distal end of the capillary vessel, or vessel itself thereby forming a standing droplet.

Under the term "liquid feed" herein is to be understood any feed comprising a solvent or blend which is a fluid at the conditions of the process. The sample may be a liquid feed comprising dissolved components, or components that are suspended or emulsified in a liquid medium.

The device according to the invention employs a first tubular vessel having as an outlet a distal end or a channel suitable for the formation of a droplet of a first volume.

The term "tubular" vessel herein refers to an essentially tubular structure that comprises an outer surface, an inner surface and a lumen at the inside of the structure. The cross-sectional shape of the tubular wall structure may be circular, or square, or of a non-specifically defined geometry. The specific geometry of the cross-section is not considered as relevant, provided that the tubular device is suitable for transferring fluids, such as for instance also applicable for channels etched in a microfluidic chip.

The tubular vessel has a defined lumen through which the solvent and sample are pumped.

Preferably, the tubular vessel is a capillary tube having an inner diameter of less than 5 mm, measured as the diameter between the largest distances.

Suitable wall materials are essentially inert with respect to the solvents and/or the components carried in the liquid feed, and are further not deformed at the temperatures or conditions employed in the subject device. Typical materials include silicon, metals and/or alloys such as gold, copper or stainless steel, glasses and thermoset polymeric materials such as crosslinked epoxy resins, poly methyl methacrylate, cyclo-olefin (co)polymers, polyimide, fluoro-ethylene polymer and/or polycarbonate.

The device according to the invention preferably further comprises means to adjust at least two of $r_1$, $r_2$ and/or $r_3$. Preferably, the device comprises means to adjust pressure, temperature and/or gas flow rate at the gas/liquid interface of the droplet. Additionally the vessel leading to the distal end may be heated to pre-heat the solvent going into the droplet and aid a more rapid evaporation process.

Preferably, in the device according to the invention, $r_1$, $r_2$ and/or $r_3$ are controlled by an automated system. Preferably, the automated system comprises at least one or more sensors, and/or one or more actuators.

The device according to the invention further preferably comprises a comparison means that correlates sensor data to a set point value, and delivers an adjustment signal to an actuator to adjust the magnitude of the parameter controlled by the actuator, wherein the actuator controls evaporation rate $r_2$.

The term "actuator" herein refers to any suitable means to control any of the controllable parameters of the system, e.g. temperature, pressure, flow rate of the liquid feed, which result in controlling of solvent evaporation rate $r_2$. The term "sensor" herein refers to any suitable means for measuring a parameter of the system, e.g. temperature, pressure, flow rate of the liquid feed.

Preferably, the automated control system comprises a machine vision unit that sequentially acquires one or more images of the droplet, processes the acquired images to determine one or more droplet parameters; and communicates the parameters to a comparison means. One or more droplet parameters include the surface integral and/or the diameter of a droplet, which at a given droplet shape can be linked to the droplet volume.

The device and arrangement according to the present invention preferably operate in an automated, or closed loop manner.

FIG. 1 discloses a preferred operating principle for such an operation. Herein, in a device (1) comprises a liquid feed input (IN) and a concentrated droplet output (OUT), an actuator (2) influencing any of the parameters relevant for $r_1$, $r_2$ and/or $r_3$, such as temperature, pressure, gas and/or liquid flow. The actuator is driven by an adjustment signal (7) which is derived from a comparison means coupled to a sensing means (5) and a set/reference means (6). The sensing means may be any suitable detector, or a machine vision means; the set/reference means representing the desired value. The comparison means may then calculate values, preferably employing suitable algorithms, and/or compare values in a look-up table with those measured by the sensing means (6). The comparison means preferably may compare two values measured at different process times, e.g. two different droplet surface areas, and then calculate based on the values the actual rates versus the desired rates, to determine the actual status versus the desired status.

The comparison means then sends an adjustment signal (7) to the actuator (2). The adjustment signal may then control the parameters of the system such that the desired evaporation is achieved, e.g. pressure, temperature, gas and liquid feed flow. The comparison means may advantageously be a computer with a suitable software programme being executed thereon.

The liquid feed composition may be controlled via a further sensing means (4), e.g. preferably a sensor detecting the presence of certain components in the feed. The gas out flow (3) may be controlled and measured as well by sensing means, e.g. measuring the thermal conductivity of the gas. The system may further comprise different sensors (not shown) at any suitable position in the device to allow additional measurements.

This ideally also contains a computing unit that is equipped with the necessary means for acquiring and interpreting the pictures taken, for calculating the droplet volume, and for controlling both the eluent flow rate as well as the evaporation rate through control of the gas flow, eluent pre-heat temperature and/or heater unit. In this way, droplet size and evaporation rate may be linked to each other, and controlled and monitored to match the eluent feed rate of the primary column.

The monitoring preferably is performed by the droplet or meniscus being monitored by a camera set-up. Preferably the camera setup is coupled with a computer running a machine-vision programme capable of monitoring droplet size, droplet colour, droplet growth, and/or meniscus position.

Preferably the computer is also coupled in a feedback mode to the heater, thus controlling droplet growth and/or meniscus position. More preferably, the machine vision programming is capable of monitoring artefact occurrence such as precipitation, discolouring, droplet fall-off, droplet distortion, air bubble formation in the droplet, crystal formation, boiling or other effects that occur during the evaporation. Preferably, visual information of droplet formation, the evaporation process and the transference process that is monitored by a camera set-up is stored on the computer for validation check up of the experiment. Yet more preferably the method for image analysis comprises pixel count, line integral, edge detection and/or curve fitting.

Alternatively, the droplet or meniscus is monitored by other measurement techniques, such as capacitive, conductive, refractive index, or mass monitoring. This preferred embodiment may be used in a constant droplet-size mode, preventing for instance dry-cooking of the sample. In this constant droplet size mode, a droplet will be maintained at a certain defined volume, whereby the evaporation will increase the amount of solute in the droplet.

The subject device and arrangement may be employed to simply control the formation of liquid volumes, e.g. if only samples that likely contain desired compounds are being evaluated, while others not containing these compounds are removed immediately. This is the case if $r_2$ is close or equal to 0, such that $r_1$ becomes equal to $r_3$. An example of such a process is one where several compounds have been separated by an LC process.

Subsequently, only those droplets containing the desired compounds may advantageously be subjected to solvent evaporation, while the remainder of the droplets may be discarded. The presence of the desired components may advantageously be determined by a sensor or detector, either prior to the subject device, or in the subject device.

The feed comprises the components in a diluted form, i.e. in a dissolved or suspended state in a first solvent or a solvent blend. The first solvent or solvent blend comprises solvents that are useful as moving phase or eluents in the first separation process.

Suitable eluting solvents, also referred to as eluents, for use in the present invention include, but are not limited to water, such as deionized water, and primary alcohols, such as methanol and ethanol; aqueous or alcoholic solvent mixtures, such as, for example, hexane/isopropanol/acetonitrile. Eluent combinations suitable for certain columns and separations are well known in the art. Additional suitable eluents can be used and techniques to determine such eluents are known to those of skill in the art. An explanation of eluents and moving and stationary phase is given in the "Adsorptive Separation" section of the Kirk-Othmer Encyclopedia of Chemical Technology.

The solvent may advantageously comprise at least one keeper solvent. By the term "keeper solvent" herein is understood a solvent which will essentially not evaporate during the process, i.e. one or more solvents or chemical component of sufficiently low volatility under the conditions of the process. In terms of the earlier defined flows in formulas I, IIa and IIb, a keeper solvent is defined as a solvent wherein $r_2$ is essentially zero. Thus the formula for a keeper solvent reduces to formula III:

$$r_1 = r_3 \tag{III}$$

Furthermore, it is understood that the keeper solvent may be present in at least an amount sufficient to retain the components in the analyte samples in a liquid state, either dissolved, dispersed and/or suspended; during and after the evaporation process, thereby preventing the sample concentration process from going to dryness. The keeper solvent hence preferably minimizes the risk of evaporation of volatile or the risk of degradation of thermally instable components in a sample fraction.

The keeper solvent may furthermore be a composition of one or more normally solid compound(s), one or more normally liquid compound(s), and/or one or more normally gaseous compound(s), which is/are liquid under the process conditions. Typical preferred compounds include ethylene glycol, propylene, glycol, glycerol, water, DMF, DMSO; long-chain alcohols, such as 1-hexanol or 1-octanol, hydrocarbons, e.g. n-alkanes such as octane, decane or tetradecane; higher hydrocarbons such as hydrocarbon waxes; silicone oils or others, as applicable; or normally gaseous, e.g. carbon dioxide, which may act as keeper solvent under supercritical conditions. The keeper solvent furthermore preferably has an essentially low normal volatility, i.e. a high boiling point and/or low vapour pressure under the processing conditions. Furthermore, the keeper solvent should essentially not interfere negatively with the separation process in the first stage, and preferably also not during the second stage. Yet further, a keeper solvent should be inert towards the analyte components.

The keeper solvent may furthermore be a deuterated species in the case that an $^1$H-NMR method is to be employed after the solvent evaporation, thereby reducing the need for larger amounts of deuterated solvents as eluents, and permitting to perform an easy solvent switch.

The keeper solvent may preferably be present in the solvent or solvent blend in any suitable amount to achieve the desired objective. It may be present as part of the first solvent or solvent blends, and/or it may added to a sample droplet prior to or during the evaporation process.

Generally, in the case of coupled chromatographic processes, such as LCxLC, the first and second solvent mixture are intended to provide orthogonal separation behaviours. For instance where a highly polar solvent or solvent blend is employed as eluent in the first separation, the second column will require an apolar solvent or solvent blend. In existing LCxLC systems, the presence of remaining solvent in the sample causes an issue with the polarity of the second separation, thereby reducing the resolution of the secondary separation. Accordingly, the first and second solvent or solvent blends at least differ in polarity.

Preferably the solvents may also be useful for a different analytical or separation method, for instance if an NMR system is coupled to the subject apparatus, the second solvent blend may be a deuterated solvent, allowing to reduce the amount of deuterated solvent required in the system, or in the case of e.g. a bioassay, solvents are evaporated that are harmful for the effectiveness of the method.

Flow rates $r_1$ and $r_2$ may advantageously be determined as follows: The in-flow into the tubular vessel can be determined, for instance through the use of a calibrated pump, or other means that measure and control the actual flow. If a second mass flow, either $r_2$ and/or $r_3$, is determined, the missing mass flow rate, respectively, can be calculated to allow control of the complete evaporation process.

The determination of $r_2$ and/or $r_3$ may be done by a variety of sensors, comprising gravimetric determination, optical detection methods, methods using electromagnetic radiation, conductimetric determination, and others.

If preferably the evaporation is done by a heated gas flow, a gas flow sensor, for instance a mass flow sensor may be positioned in the effluent gas stream leading the evaporated solvent away from the heating area, which after calibration can be used to determine the exact amount of solvent removed.

Another preferred method may use a method to determine the size of the droplet, by for instance the deflection of a laser beam passing through a hanging droplet. Still another preferred method comprises use of a camera to obtain pictures of a hanging droplet or meniscus. By determining the size and position of said droplet, droplet sheet or meniscus, the volume of the remaining liquid may advantageously be determined. When two determinations are done in succession over a known time period, this permits to determine the mass flow rate into the remaining liquid volume.

In a particularly suitable method, the camera element is attached to a computer system which analyzes the images taken, and uses an algorithm to calculate the size and position of the droplet, meniscus and/or sheet, e.g. by integration of the pixel count corresponding to a surface area.

An advantage of such a method is that the camera system does not need to be calibrated for volume measurements.

This determination of the other flows may preferably be done with a sensing system which determines the outflow of evaporated gases. Another preferred option comprises a sensing system which determines the volume of liquid present in the evaporation zone, specifically in the case of a pendant hanging droplet or a droplet sheet, or which determines the position of a liquid meniscus.

Generally, many different sensing systems may suitably be used to determine the size of a hanging droplet or droplet sheet. These sensing systems may detect directly, for instance by non-contacting means as in an optical system.

The sensing systems may advantageously be based on electromagnetic principles, optical principles, mass principles, acoustic principles, mechanical principles, thermal principles and/or other principles known to people skilled in the art.

However in case such sensing systems are dependent on the bulk solution properties of the liquid in the droplet, e.g.

refractive index, optical absorbance or transmission, electrical or thermal conductivity such sensing systems will not only measure a signal resulting from the size of the droplet, but also of the changes in the bulk properties of the droplet during the whole process. As such these sensing systems will determine 'real' signal components corresponding to the droplet size, but also a 'parasitic' signal component corresponding to the droplet bulk properties. The parasitic signal component may result in erroneous behaviour of the control system which steers the evaporation process. Examples for occurrences that may result in a parasitic signal include refractive index changes, the crystallisation of compounds in a droplet, and phase changes of emulsions or dispersions.

Preferably, therefore, the system according to the invention therefore uses sensing systems which are relatively insensitive to the abovementioned solvent bulk properties, such as a system comprising a camera system with image recognition and image processing, i.e. machine vision capabilities.

The machine vision system may be employed to generate a control system for the evaporator module in which the droplet is present.

The camera system preferably may then detect the size of the droplet and sends a signal to increase the evaporation rate in case the droplet grows in size and sends a signal to decrease the evaporation rate in case the droplet decreases in size. In case the droplet volume is the same as the 'set value' the control signal is held constant. If the machine vision system is fast, i.e. performing many image acquisition and processing cycles per time period and if the evaporator module is fast the evaporation of the droplet can be controlled adequately.

Preferred options for image processing include measuring the boundary of the droplet and the background to obtain a characteristic length scale of the droplet, e.g. radius and/or diameter. Another preferred option is to determine the integral area of the droplet, e.g. the number of pixels.

As set out above, an advantage of using machine vision resides in the fact that machine vision is relatively independent of the bulk properties of the liquid in the droplet. This is particularly beneficial where during the total duration of the process, changes in the liquid composition may occur as for instance in a 'gradient-run' in liquid chromatography. During a gradient run, a mixture of two or more solvents, which is used as the eluent, is changed during time. For instance a chromatographic run may start at a ratio of 10% wt. water to 90% wt. methanol blend, and may change over a time period to 100% wt. water and 0% wt. methanol. Such a gradient run is common in analytical applications where it is used to decrease chromatographic run time.

Independently of whether a closed or open system is employed, in step a) a droplet is formed. This is achieved by passing the fluid sample through the lumen of the tubular vessel until the droplet is formed at the distal end of the tubular vessel. The droplet will have a first defined volume, which corresponds to a defined surface area, and, at a given geometry to a defined diameter.

The droplet may thus be defined by its diameter, surface area and/or volume, all of which are functions of the surface tension at the gas/liquid boundary, and of the shape of the tubular vessel.

If a droplet is supposed to be transferred to a receiving means, or if a droplet is supposed to be disposed of, the droplet preferably is a pendant, i.e. freely-hanging droplet, balanced by the equilibrium between upward tubular vessel and surface forces and downward gravitational forces. Droplets of up to 15 µL volume have been shown to successfully hang at a tubular vessel exit before gravitational forces become larger than the upward forces.

However, the droplet may have a different, smaller volume. Preferably the droplet comprises of from 0.001 to 15.0 µL, more preferably of from 0.01 to 14.0 µL, yet more preferably of from 0.1 to 5.0 µL of liquid feed.

If the droplet is a pendant droplet, it will usually have a diameter of less than 500 µm diameter. The volume and the diameter are linked by a cubic function relative to the diameter: while a droplet with a 50 µm diameter represents a volume of 65 picoliters, a 500 µm diameter drop represents a 65 nanoliters volume.

Figures 2A, 2B, 2C, 2D, 2E:
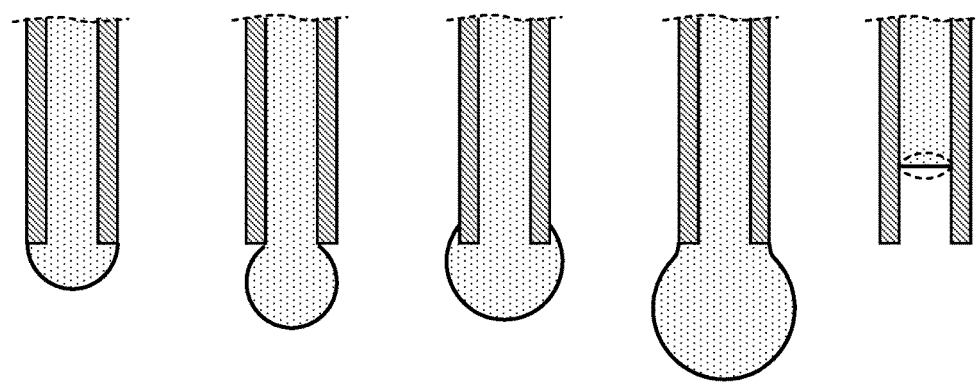
FIG. 2 a) to e) disclose cross-sectional views of various preferred embodiments of a tubular vessel, and the droplet formed at the tip, or inside the vessel.

The droplet may have a spherical shape or a meniscus shape, or an elongated droplet sheet shape, or any shape between the three. The spherical shape is most preferred, since it has the advantage that when evaporating the solvent in a spherical droplet, the surface to liquid volume ratio is maximally increased, maximizing the evaporation rate, whilst minimizing analyte adsorption. FIG. 2 illustrates a number of different shapes and position that a droplet may form in a device according to the invention. FIG. 2a shows a droplet having a meniscus shape extending below a tubular vessel. The droplet outer perimeter wets the outer side of the tubular. FIG. 2b illustrates a pendant droplet that is hanging from the inside of a tubular vessel. FIG. 2c shows a pendant droplet that is wetting the outside of the tubular vessel, while FIG. 2d shows a larger pendant droplet that is pending from the outside of the tubular vessel tip. FIG. 2e finally shows a droplet that may be formed in a tubular vessel, e.g. in a closed system. Herein, the liquid feed may either form a concave or a convex meniscus with respect to the gas liquid barrier, or essentially for a flat surface. The actual shape largely depends on the forces active in such a system, the tubular vessel dimensions, the surface tension of the tubular vessel, and the viscosity of the liquid feed.

In any case, if the boundaries are known such as the size of the tubular vessel, the diameter and shape, and hence the volume of a droplet may advantageously be determined from the diameter and shape of a droplet.

In a preferred embodiment, the pendant droplet volume is kept constant and gradient runs are performed automatically. This greatly reduces the solvent evaporation parameter complexity. In this case, the droplet size may preferably be continuously maintained, in the so-called constant droplet size mode.

If the volume or evaporation rate of the solvent blend is changing through the process, e.g. at a solvent gradient, the droplet volume is preferably continuously monitored.

While this may be performed by all suitable optical means, such as a photodiode and laser or focused light beam set-up, due the difference in droplet shape that may occur in a single run, the monitoring is preferably performed via a machine vision setup that is coupled to a heater/gas flow unit in a feedback modus, the heater/gas flow unit providing the defined gas flow.

The device according to the invention further preferably comprises a means for dispensing the droplet from the distal end or within the lumen of the tubular vessel.

The device according to the invention further comprises a means (c) for diluting the concentrated sample droplet in a second solvent or solvent blend to obtain a re-diluted sample.

The present invention further relates to an arrangement for the multi-dimensional separation of a liquid feed comprising one or more components wherein the device is employed. The arrangement preferably comprises i) at least a first separation device for the separation of components diluted in a first solvent or solvent blend in a first dimension into a first liquid feed; and ii) a device according to the invention for selective solvent evaporation from the first liquid feed to obtain one or more concentrated droplets, and iii) a device for analyzing the components in the concentrated droplets. Preferably, the device for analysing the components in the concentrated droplets may comprise a physical and/or chemical analysis tool. This allows to integrate the separation method directly with a suitable analysis tool, which is highly desirable for instance for analytical devices typically employed in medical laboratories that perform serial analysis.

The present invention further relates to a process for the selective solvent removal from a liquid feed comprising one or more components diluted in at least a first solvent or a solvent blend, as set out above.

In this process, the droplet preferably has a defined volume, with a first defined surface area.

The present process preferably separates components that are less volatile than the solvents employed.

Components that have a higher vapour pressure than one or more of the solvents, will likely be removed at least in part during the evaporation step. These can however be advantageously retained in the effluent gas flow, for instance by installing a cold trap. Furthermore, the presence of such components can be monitored indirectly through a change in the required heating power, which can indicate the presence of such components. This is beneficial since it indicates reliably the presence of low boiling components that may require a different determination method.

The process is preferably continuously adjusted, by means of measuring various parameters, such as volume, shape, effluent gas composition, effluent gas flow rate, temperature and/or pressure, and adjusting one or more parameters of the device that control the evaporation and/or inflow rate.

The influence of the presence of lighter components on evaporation and accumulation rate is considered initially not relevant since the components are present in a dilute form and hence will only influence the rates to a negligible extent.

Advantageously, in the process, the evaporation rate $r_2$ is equal or higher to the flow of liquid feed $r_1$ added to the droplet through the tubular vessel. As a result, the contents of the droplet becomes more concentrated overtime, which allows e.g. to operate at a higher concentration for a second separation process, resulting in more sensitive analyses.

In a particularly preferred way of executing the present process, the defined droplet volume is essentially kept constant.

While there are many suitable ways known to a skilled person to sense the droplet surface area, a particularly advantageous way is by monitoring the defined droplet surface area by machine vision, as set out herein below.

The present process may be operated in an open or in a closed set-up. In a closed system, i.e. a system that is closed with respect to gas flow and without pendant droplet, in order to control the evaporation process, the mass, volume or mole flows in the system may advantageously be determined and controlled by measurement of geometrical parameters of the fluid meniscus. Preferably, the vessel in such a closed system is transparent in a wavelength region that allows measurement of the geometrical parameters of the meniscus to be performed, e.g. made from glass or suitable transparent polymeric materials for optical measurements, or silicon for infrared measurements.

The liquid feed preferably is subjected to a first separation through CE and LC (RP, NP), the latter eventually coupled with a suitable detector indicating presence of components and/or solvents in an aliquot of the liquid feed as set out below.

Upon formation of a suitable concentrated droplet, or a re-dissolved droplet, the concentrated droplet may preferably be dispensed from the tubular vessel. The thus dispensed sample may advantageously be re-dissolved in a second solvent or solvent blend where required by a second stage. The re-dissolved sample may then advantageously serve as liquid feed for a second separation process. Alternatively, the concentrated droplet may also be redissolved immediately prior to being dispensed, e.g. if the droplet was formed inside a tubular vessel rather than at its tip, or by supplying the second solvent or solvent blend to the concentrated droplet at the tip.

The concentrated droplet may however also be subjected directly to a further separation of analysis step without addition of a second solvent or second solvent blend, e.g. when using the concentrated droplet for mass spectroscopy.

After evaporation, the droplet is preferably periodically transferred into a droplet sample reservoir which can be switched to a secondary liquid feed.

In a preferred embodiment, the droplet is transferred to and released into a sample reservoir for redissolving in the second solvent, or re-dissolved by other suitable means for adding the second solvent before introducing it into the sample reservoir.

The tubular vessel may comprise an ejection actuator that may effect a shock wave ejecting the droplets out of the liquid surface.

The tubular vessel may yet more preferably further comprise several layers, wherein one or more capillaries may be located close to the tip, e.g. concentrically around the tip of the ejection tube, where the droplet or a meniscus of dispensing liquid develops which extends beyond the tip of the ejection tube. Preferably, the outermost tubular protrudes beyond the inner capillaries in the direction of a longitudinal axis of the ejection tubular vessel.

Preferably, at least part of the surfaces of the ejection tubular wall are hydrophilic. More preferably, at least an outer surface of the tubular vessel is hydrophobic, yet more preferably through treatment or material choice, e.g. treatment with a silane such as hexamethyldisilazane.

Preferably, the tubular vessel is shaped such that there is a sharp edge between the hydrophilic interior surface side and the hydrophobic exterior surface of the outermost tubular vessel, for instance by shaping the distal end such that no or hardly any wetting by the solvent or eluent can occur at the outside, thereby minimizing the contact angle by design and/or material choice.

In step b), the droplet is subjected to an evaporation process at a defined evaporation rate. This may advantageously be performed by contacting the droplet with a defined gas flow of a carrier gas, and/or by applying underpressure, by placing a heating unit into close proximity of the droplet, and/or any combination of these. A heating unit according to the subject invention should be understood as any means providing heat or heated gas flows, either through convection, radiation or other means. In this step, at least part of the first solvent or solvent blend present in the droplet is removed at least in part from the sample, by evaporation, i.e. by boiling off or by sublimation.

The device according to the invention further preferably comprises a means for dispensing the droplet from the distal end or within the lumen of the tubular vessel.

The device according to the invention further preferably may comprise a means (c) for diluting the concentrated sample droplet in a second solvent or solvent blend to obtain a re-diluted sample.

The present invention further relates to an arrangement for the multi-dimensional separation of a liquid feed comprising one or more components wherein the device is employed. The arrangement preferably comprises i) at least a first separation device for the separation of components diluted in a first solvent or solvent blend in a first dimension into a first liquid feed; and ii) a device according to the invention for selective solvent evaporation from the first liquid feed to obtain one or more concentrated droplets, and iii) a device for analyzing the components in the concentrated droplets. The present invention further relates to a process for the selective solvent removal from a liquid feed comprising one or more components diluted in at least a first solvent or a solvent blend, as set out above.

In this process, the droplet preferably has a defined volume, with a first defined surface area.

The present process may be operated in an open or in a closed set-up. In a closed system, i.e. a system that is closed with respect to gas flow and without pendant droplet, in order to control the evaporation process, the mass, volume or mole flows in the system may advantageously be determined and controlled by measurement of geometrical parameters of the fluid meniscus. Preferably, the vessel in such closed system is transparent in a wavelength region that allows measurement of the geometrical parameters of the meniscus is performed, e.g. made from glass or Perspex for optical measurements, or silicon for infrared measurements.

The liquid feed preferably is subjected to a first separation through CE and LC (RP, NP), the latter eventually coupled with a suitable detector indicating presence of components and/or solvents in an aliquot of the liquid feed as set out below.

As a result of the subject process, a concentrated sample is obtained, either neat or in a solvent remnant. The solvent blend in the droplet may change during this process, e.g. by azeotropes formed, thereby resulting in a solvent gradient over time.

This concentrated sample is then preferably diluted with a second solvent or solvent blend, to obtain a re-dissolved sample.

The re-dissolved sample droplet is then preferably transferred into a sample receiving means for receiving an aliquot of the fluid re-dissolved sample. Step c) may preferably be combined with this transfer step.

Preferably, the device according to the invention comprises an embodiment for droplet release for transport to, or insertion into a subsequent separation or detector instrument.

Upon formation of a suitable concentrated droplet or a re-dissolved droplet, the concentrated droplet is preferably dispensed from the tubular vessel. The thus dispensed sample is then preferably re-dissolved in a second solvent or solvent blend. The re-dissolved sample may then advantageously serve as liquid feed for a second separation process. Alternatively, the concentrated droplet may also be re-dissolved immediately, e.g. if the droplet was formed inside a tubular vessel rather than at its tip, or by supplying the second solvent or solvent blend to the concentrated droplet at the tip.

The first tubular vessel is preferably attached to a translation means through which the re-dissolved droplet can be brought to or into contact with said receiving unit. In the case of a pendant droplet, the receiving means is preferably positioned underneath the tubular vessel and/or the droplet, such that a released droplet falls into said receiving unit through gravity.

More preferably, the droplet release from the first tubular vessel is achieved by applying mechanical or electrical force, including through a piezoelectric element, a shape memory alloy, a magnetostrictive element, and/or an electrode capable of applying an electrostatic field; a gas pulse, laser pulse, knife, hydrostatic shock, electrostatic shock, wicking, capillary action, and/or differential pressure.

The receiving means or reservoir may be a second tubular vessel whereby the droplet may be transferred through coalescence, the droplet may be dipped into a cup-shaped reservoir, which preferably may be assisted by suction; by coalescence with a second droplet of the second solvent; it may it may be dripped off in a controlled way or it may be ejected, e.g. by a shock wave generated through pressure difference in the tubular vessel, by contacting the first tubular vessel with a piezoelectronic device that activates a shock wave.

The sample receiver is preferably connected to a second tubular vessel for sequential analysis and separation, this may advantageously include a valve or fluid switch for adding solvent to this sample volume, as disclosed in Hongzhe Tian et al. as described herein-above.

Preferably, in the apparatus according to the invention, the first tubular vessel means may represent the outlet of a first chromatographic separation unit, wherein the unit may consist of a chromatography column, a solid-phase extraction column and/or the outlet of an electrophoresis column. More preferably, the first tubular vessel may be directly connected to the inlet of a detector, such as a UV detector, and/or fluorescence detector.

The receiving means preferably comprises a receiving surface, preferably shaped as a well, reservoir, tube, channel, tubular vessel or inlet.

More preferably, the apparatus comprises at least a first receiving device with a plurality of receiving units that may receive a plurality of droplets.

Preferably, this receiving device comprises a translation means to which a receiving unit is attached, such as to receive sample droplets. The translation means may comprise, preferably, a MALDI plate, a multi-well plate, a hybridization plate and/or a Lab-on-a-Chip.

The re-dissolved or re-diluted and/or enriched sample may also be preferably introduced into a second separation and/or analytical method, such as, but not limited to separation and/or analytical techniques including LC such as RP, NP, TLC; CE, NMR, MS, UV/VIS, nano LC, HPLC, UPLC; RP-(UV/VIS)-EV-NP-MS; RP-(UV/VIS)-EV-NMR; NP-(UV/VIS)-EV-CE-MS/RP-(UV/VIS)-EV-CE-MS; RP(UV/VIS)-EV-TLC/NP-(UV/VIS)-EV-TLC; EV-nano LC and CE-EV. The present invention therefore advantageously also relates to a process combining any of these methods with a first separation method, and a sample concentration or simply solvent switch step. The EV can also combine to sample preparation methods prior to the next analysis. Also the EV can serve as an injector interface to transfer samples in a suitable for into a subsequent analyzer.

The receiving means further preferably comprises a valve, wherein the reservoir may form part of the inlet of the valve in which the droplet is released. Then the valve facilitates transfer of the sample to a subsequent separation or detector instrument.

The apparatus also preferably comprises a means for waste liquid disposal, such as a tube, well or absorbent material to which a droplet can be transferred that is not of interest for further analysis.

The heating means preferably comprises a heat-source for heating up the gas around the droplet, or an irradiation unit that is heating up the droplet directly. Also a heating means may preferably be present which is used to pre-heat the solvent going into the droplet. In the case of a capillary vessel with a distal end holding a droplet, a heating element is positioned around the capillary vessel to heat the internal liquid feed.

Preferably the droplet or meniscus is enclosed in a partially enclosed chamber that assures laminar air-flow along the droplet to enclose the heated space and assures removal of evaporated compounds. This partially enclosed chamber preferably has a bell shape or (frusto)conical shape with a continuous reducing radius, wherein an opening is arranged on an upper part to assure outlet of gas and an opening on lower part to assure transfer of the droplet for downstream processing and fresh gas influx.

Preferably, the heater comprises one or more coils, wires or patterned metal lines on a substrate, which more preferably are positioned such that transfer of the droplet to a next channel, surface, well, reservoir, tube, tubular vessel or inlet is facilitated.

FIGS. 3a and b illustrate such a preferred setup. A sample is herein eluted from the distal end of a capillary, forming a pendant droplet or a meniscus, which is evaporated concurrently by an external heater. The droplet is freely-hanging, balanced by the equilibrium between upward capillary and surface forces and downward gravitational force.

The receiving means also may be preferably connected to a second tubular vessel placed in the direct vicinity of said first tubular vessel, such that the droplet can be brought into contact with a second droplet, containing eluent of different or same composition as eluent in the eluate coming from said first tubular vessel.

In a preferred embodiment, the droplet size is continuously monitored by a machine vision setup that is coupled to the heater in feedback modus. In this way, droplet size and evaporation rate is controlled and monitored to match the eluent feed rate of the primary column. The evaporated sample volume is kept constant and gradient runs are performed automatically.

Figure 3:
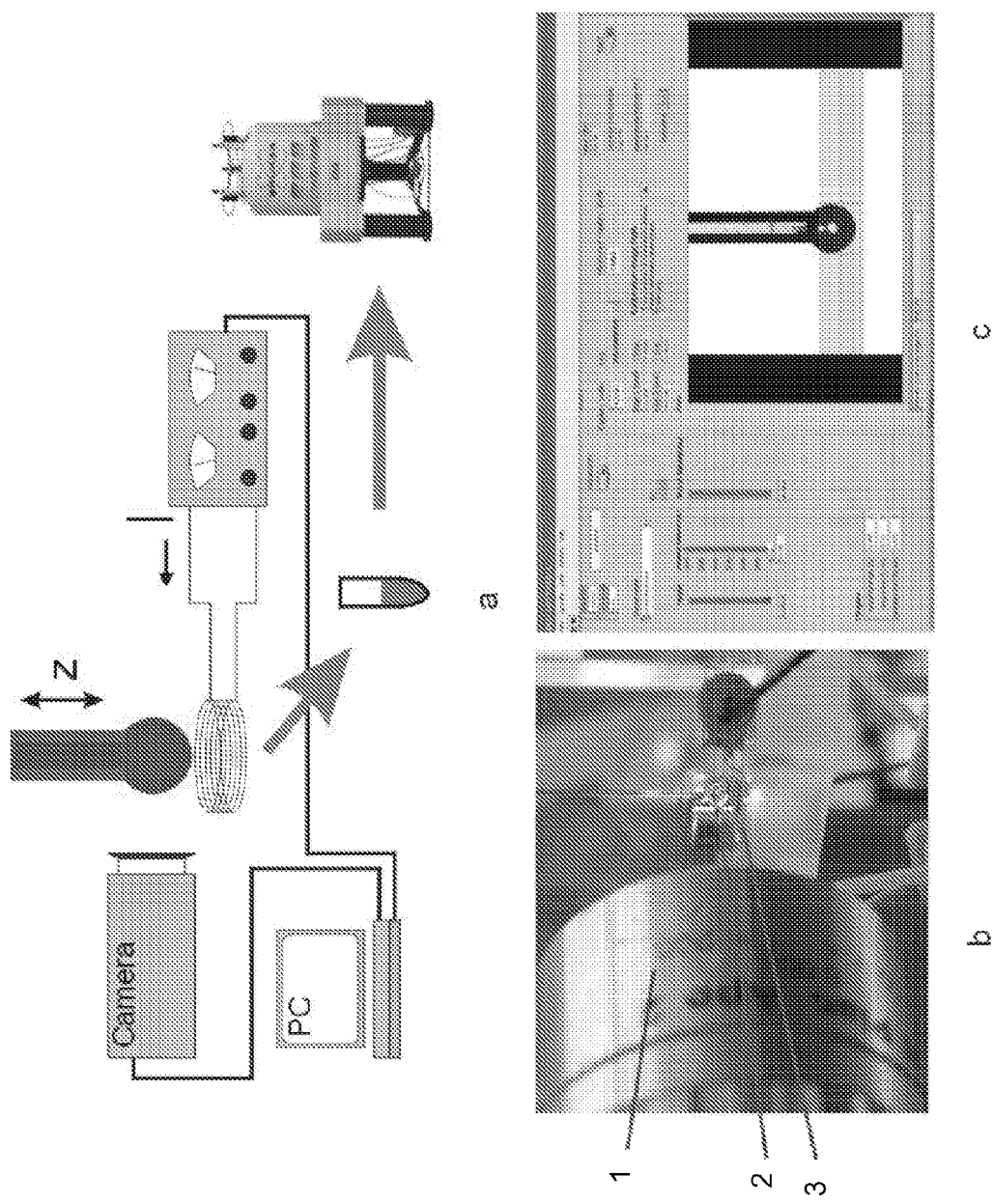
FIG. 3 shows a schematic overview of a preferred arrangement according to the invention for NMR characterization of evaporated LC samples: a) a pendant droplet from a capillary is evaporated using a current controlled heating coil. The droplet is kept at a constant volume by a computer controlled machine vision feedback loop. The droplet is transferred into a vial using a translation of the capillary, followed by analysis in the NMR machine. b) Close-up of a pendant droplet. c) Computer interface for monitoring the droplet and keeping it at constant volume through feedback.

FIG. 3 a-c illustrate a preferred embodiment of the present process. Herein, the pendant droplet size is monitored continuously by a machine vision setup that is coupled to the heater in feedback modus. In this way, droplet size and evaporation rate are controlled and monitored to match any isocratic or gradient eluent feed of the primary column. The setup is used in a constant droplet-size mode, preventing dry-cooking of the sample. After evaporation, the droplet is transferred to and released into a vial that contains 100 μL deuterated NMR solvent.

After evaporation, in this preferred embodiment, the droplet may be transferred to and released into a sample reservoir inside which is part of a valve. The valve preferably has a dedicated design to suit small droplet volumes (e.g. 50-500 nL), whereby these volumes are 25-100 times smaller as those reported in prior art. As a result, it is expected that even a remainder of solvent in the droplet would not deteriorate the chromatographic separation, due to reduced solubility problems, less interference towards stationary phase and other effects.

The sample reservoir preferably also enables accurate and constant injection volumes which due to the small dimensions decrease the peak band broadening effects as well as enables the transition between low and high pressure region, e.g. 1 and 200 bar, which is needed to perform a second separation step.

A fast second dimension separation is preferably applied because preferably the first dimension separation is not halted. Halting the first dimension separation will lead to band dispersion and a significant reduction in the quality of the first dimension separation. The subject process therefore preferably operates at a concentration of components whereby the solvent evaporation rate remains predominant. Preferably the process operates under conditions whereby more than 75% of the overall evaporation rate is contributed by the solvent or solvent blend.

The subject device and process may advantageously be employed in separations followed by a bioassay, such as an immuno assay or enzyme assay. Since in these assays the components and kit components (e.g. reaction vessels) are usually sensitive to solvents, it is preferred that essentially any inhibiting solvent is removed from the concentrated droplet prior to the assay.

Experimental Part

The following non-limiting examples illustrate the usefulness of the present invention.

Example 1

Hyphenation of Liquid Chromatography and NMR

In this example, controlled evaporation of a pendant droplet that is kept at constant volume using an automated machine vision controlled feedback loop is used to exchange non-deuterated solvent employed as eluent for the LC with a deuterated solvent. Herein, two fractionated tomato samples, a whole carrot extract and an academic mixture of polyphenols are evaporated selectively, followed by NMR analysis (see table 1 for the samples used).

TABLE 2

Summary of samples

| No. | Sample | Solvent | Dilution |
|---|---|---|---|
| 1 | Whole tomato extract | $H_2O$ | 1:10 |
| 2 | Fractionated tomato (amino acids) | $H_2O$ | 1:10 |
| 3 | Fractionated tomato (sugars) | $H_2O$ | 1:10 |
| 4 | Carrot extract | $H_2O$/MeOH | 1:10 |
| 5 | Polyphenol mixture | MeOH | 1:10 and 1:1 |

The polyphenol mixture comprised Epigallocatechin gallate (EGCG), a polyphenol typically present in green tea; 5-(3,4-dihydroxyphenyl)-γ-valerolactone, a gut microbial bioconversion product of polyphenols; myricetin as typically present in red wine; and gallic acid.

Evaporation Method

The arrangement of FIG. 3 was employed for this experiment. Herein, a sample was eluted from the distal end of a capillary, forming a pendant droplet or a meniscus, which was evaporated concurrently by an external heater.

The droplet was freely-hanging, balanced by the equilibrium between upward capillary and surface forces and downward gravitational forces. The droplet size was monitored continuously by a machine vision setup coupled to the heater in feedback modus. In this way, droplet size and evaporation rate were controlled and monitored to match any isocratic or gradient eluent feed of the primary column. The setup was used in a constant droplet-size mode, preventing dry-cooking of the sample. After evaporation, the droplet was transferred to and released into a vial that contained 100 µL deuterated NMR solvent. An evaporation interface for improved LC-NMR hyphenation.

The sample stock solutions were diluted ten times in their respective solvents. These diluted samples were fed into a 1000 nL droplet with a Harvard Syringe pump 22 at a feed rate of 3.0 µL/min. The emerging sample liquid evaporation rate was maintained at a constant droplet volume of 1 µL. Each 200 seconds (ten times in total) the droplet was injected into a 1.5 mL Eppendorf tube containing 100 µL of the deuterated version of the respective solvent. The total duration of the run was 33.33 min. D-solvent was added to the sample up to 250 µL.

One positive and two negative controls were performed. The positive control was prepared by pipetting 25 µL stock solution to 100 µL deuterated solvent operated at the same conditions as the evaporation runs to correct for ambient effects and sample instability. The negative controls were prepared by pipetting 100 µL of deuterated solvent in 1.5 mL Eppendorf tubes, one opened and one closed during the entire evaporation runs. Samples 3 and 5 were repeated for a 1:1 dilution in order to observe scaling effects. The samples were then transferred to NMR vials using Pasteur pipettes.

NMR Data Acquisition

1D $^1$H-NMR spectra were recorded on a Bruker Avance III 600 MHz spectrometer, equipped with a 5-mm cryo-cooled probe head. The probe was tuned to detect 1H resonances at 600.25 MHz. The internal probe temperature was set to 300 K. The spectra were acquired with pre-saturation of the water resonance using a noesygppr1d pulse sequence RD-90°-$\rho$1-90°-$\rho$mix-90°-FID (Bruker Biospin, Germany). Here, $\rho$1 is a 4 µs delay time, and $\rho$mix is the mixing time (10 ms). 64 scans were collected in 64 k data points with a relaxation delay of 30 seconds, an acquisition time of 3.63 seconds, a spectral width of 15.0 ppm (8993 Hz) and an offset of 2821 Hz (4.70 ppm).

The data were processed in TopSpin software version 1.3.10 (Bruker BioSpin GmbH, Rheinstetten, Germany). An exponential window function was applied to the free induction decay (FID) with a line-broadening factor of 0.3 Hz prior to the Fourier transformation. Manual phase and baseline correction was applied to all NMR data.

Observations and Results

Figure 4:
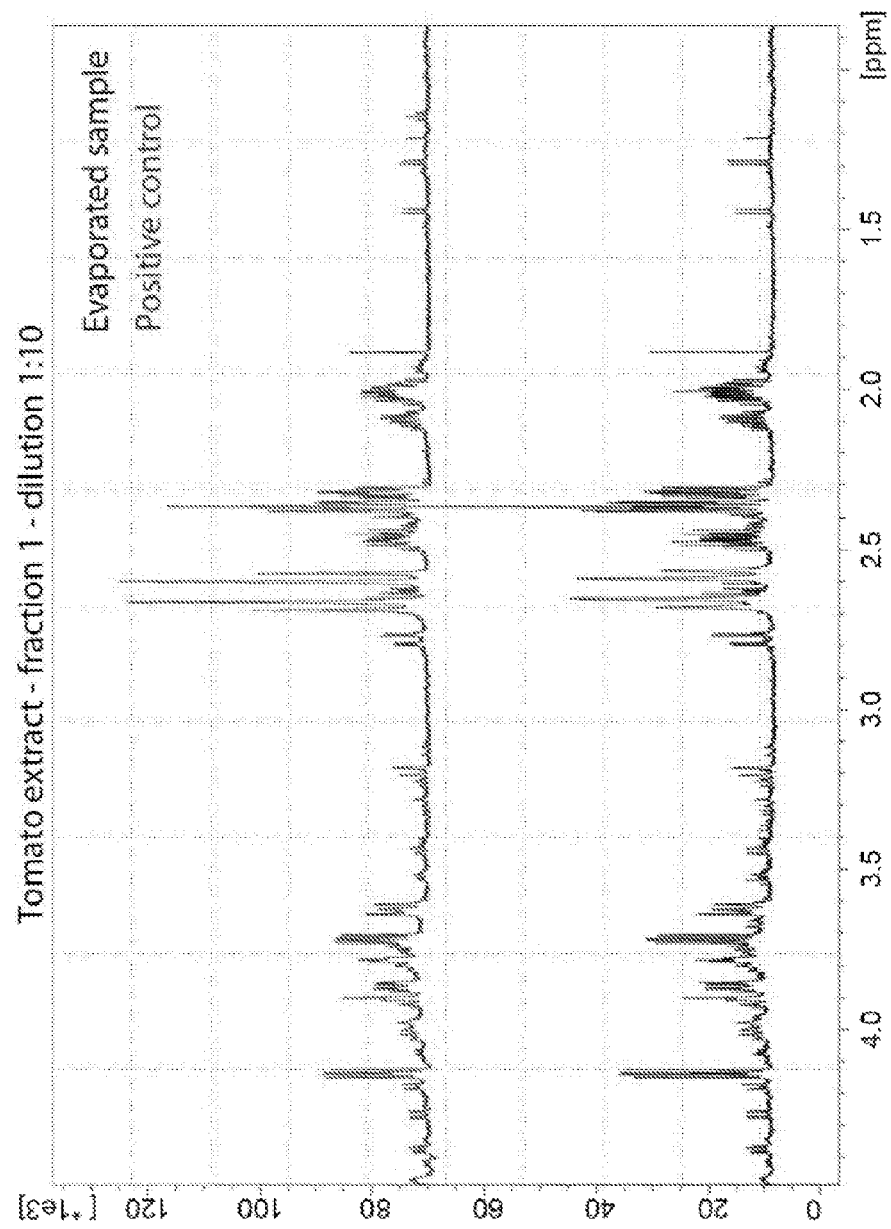
FIG. 4 is an NMR profile of an LC separated tomato extract.

FIG. 4 depicts an NMR profile of an LC separated tomato extract, containing primarily amino acids. Peaks observed include glutamic acid, glutamine, citric acid, γ-aminobutyric acid, alanine, aspartic acid and threonine. The only obvious difference that can be observed is an ethanol peak in the positive control that has disappeared during the evaporation process. The citrate peaks appear to be somewhat lower for the evaporated sample, while the left most peaks, in the region of a.o. choline, ascorbic acid, praline and phenylalanine, the peaks are higher for the evaporated sample. Interestingly, peaks for glutamic acid and glutamine appear to have shifted with respect to graphs reported in literature, probably due to differences in pH.

However as this has also happened in the positive control, this cannot be attributed to the evaporation operation.

Figure 5:
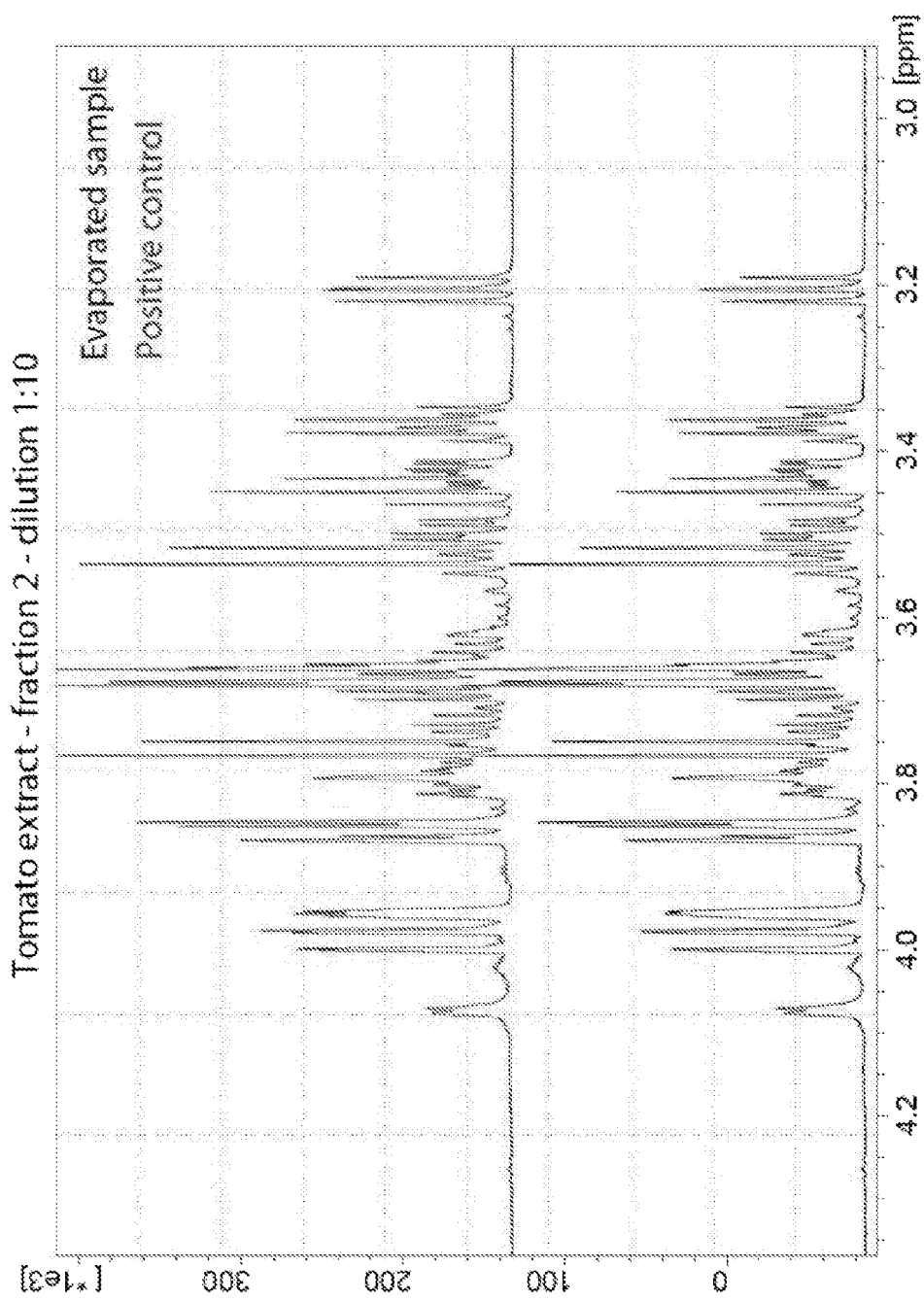
FIG. 5 shows an LC separated tomato extract at dilution 1:10

FIG. 5 shows an LC separated tomato extract containing primarily sugars. Peaks include glucose, fructose, and galactose. There appear to be no large disturbances of the profile due to evaporation. All peaks seem to be present, while shape and size are largely the same.

The benefit of the present method including an LC separation step, followed by evaporation of the solvent and NMR analysis becomes clear when comparing the regions between 3 and 4 ppm of FIGS. 4 and 5. Sugar peaks in FIG. 5 are about ten times higher than the amino acid peaks in FIG. 4.

Moreover the region is highly populated, so that specific compositional data can only be extracted in a meaningful way only after prior separation.

Figure 6:
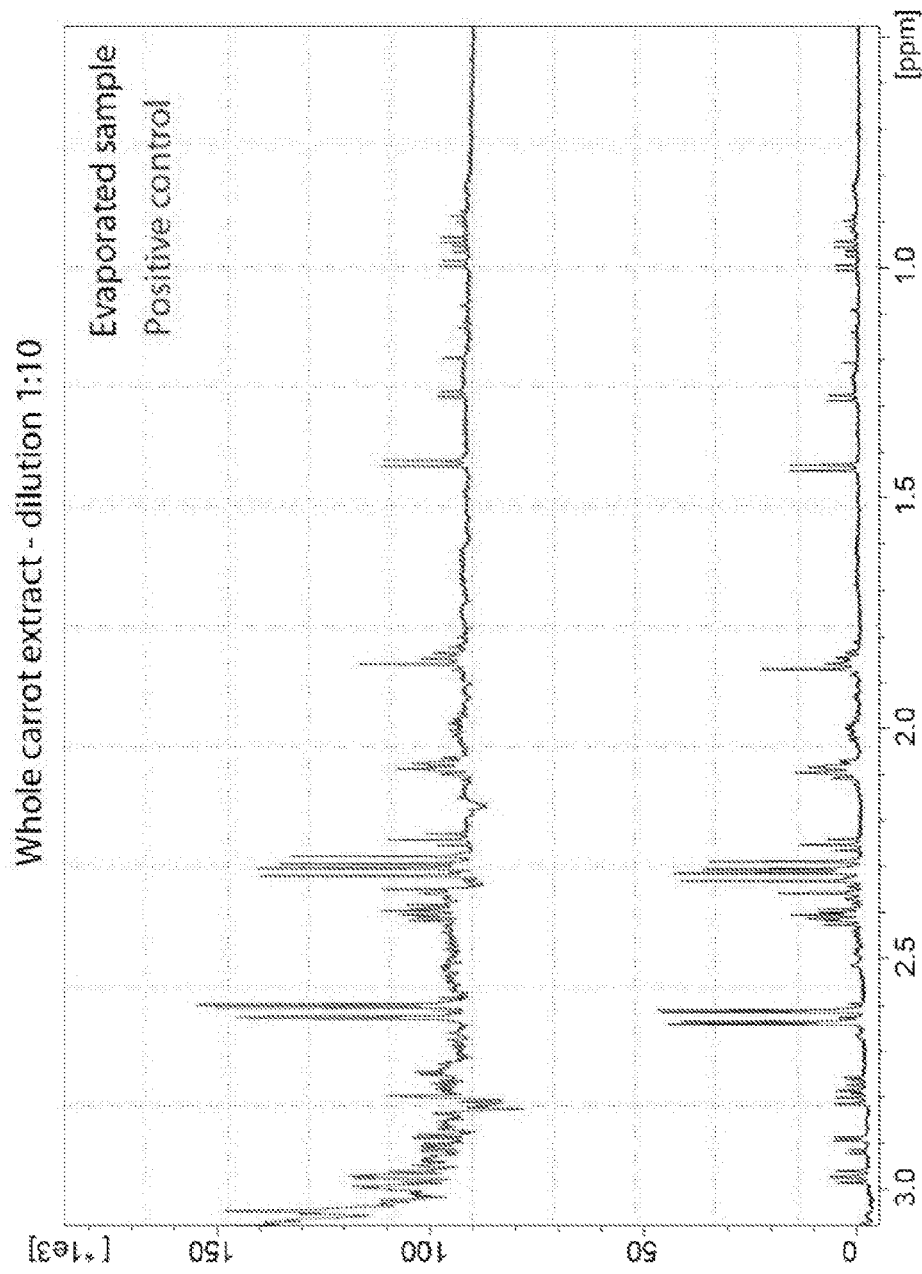
FIG. 6 shows the amino acid region of a whole carrot extract.

FIG. 6 shows the amino acid region of a whole carrot extract, i.e. the lower chemical shift region of the spectrum. The left side of the positive control shows a distorted profile due to erroneous addition of protonated methanol in the sample.

The evaporated sample precisely corresponds with literature values and is comprised of peaks for GABA, asparagine, aspartic acid, malic acid, glutamine, acetic acid, alanine, threonine, valine, isoleucine, and leucine.

Only ethanol is absent in the sample. There is also a reasonable agreement between the positive control and the evaporated sample. However the positive control is suffering from a severe methanol peak that largely disturbs the profile, while the evaporated sample did not show this methanol peak.

Figure 7:
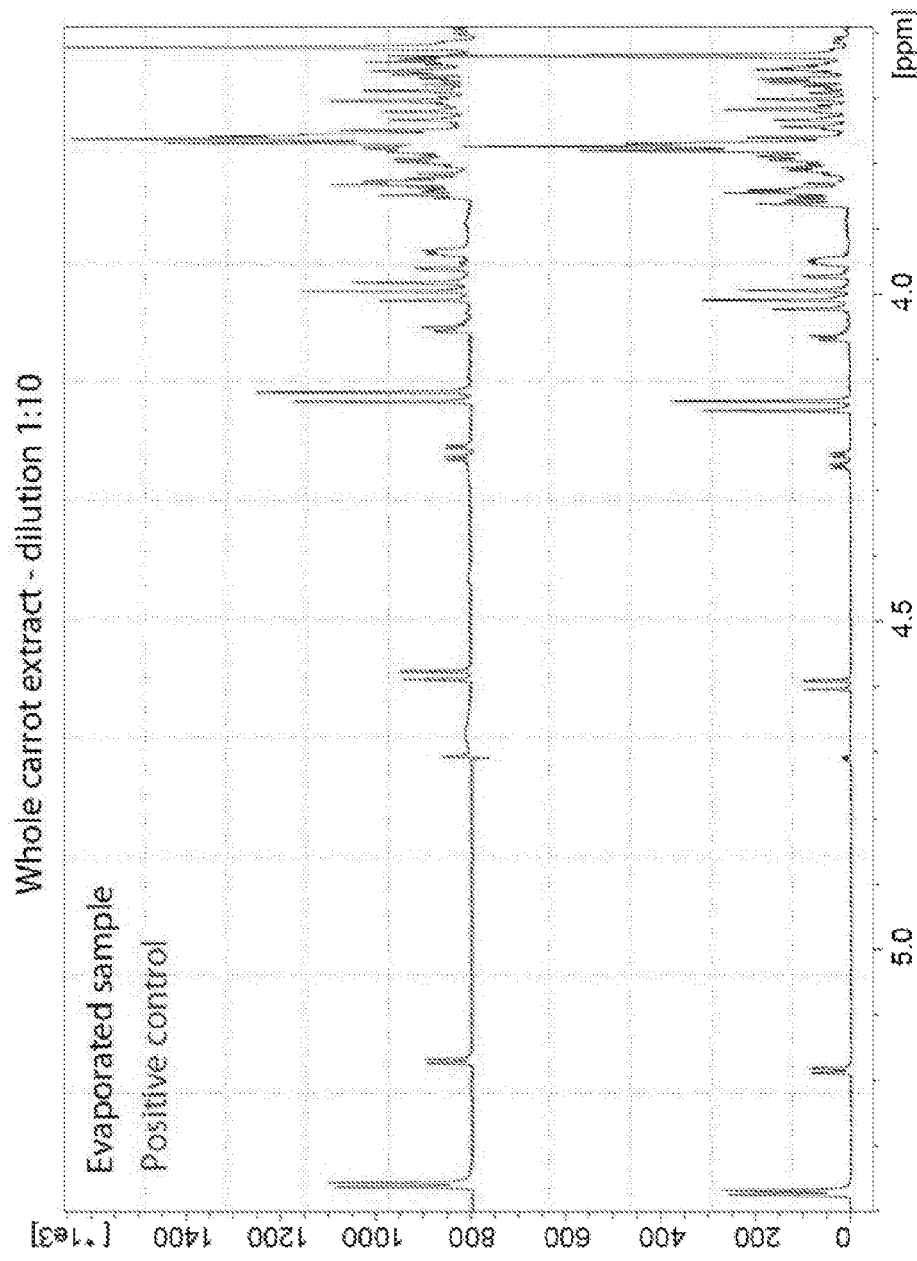
FIG. 7 shows the predominantly sugar region of the whole carrot extract.

FIG. 7 shows a region of the whole carrot extract containing predominantly sugars, i.e. the higher chemical shift region of the spectrum.

The measured values corresponded well with literature values. Furthermore, evaporated sample and positive control show no significant difference between presence or location of peaks, allowing the conclusion that no significant degradation of compounds such as amino acids and sugars has taken place.

Figure 8:
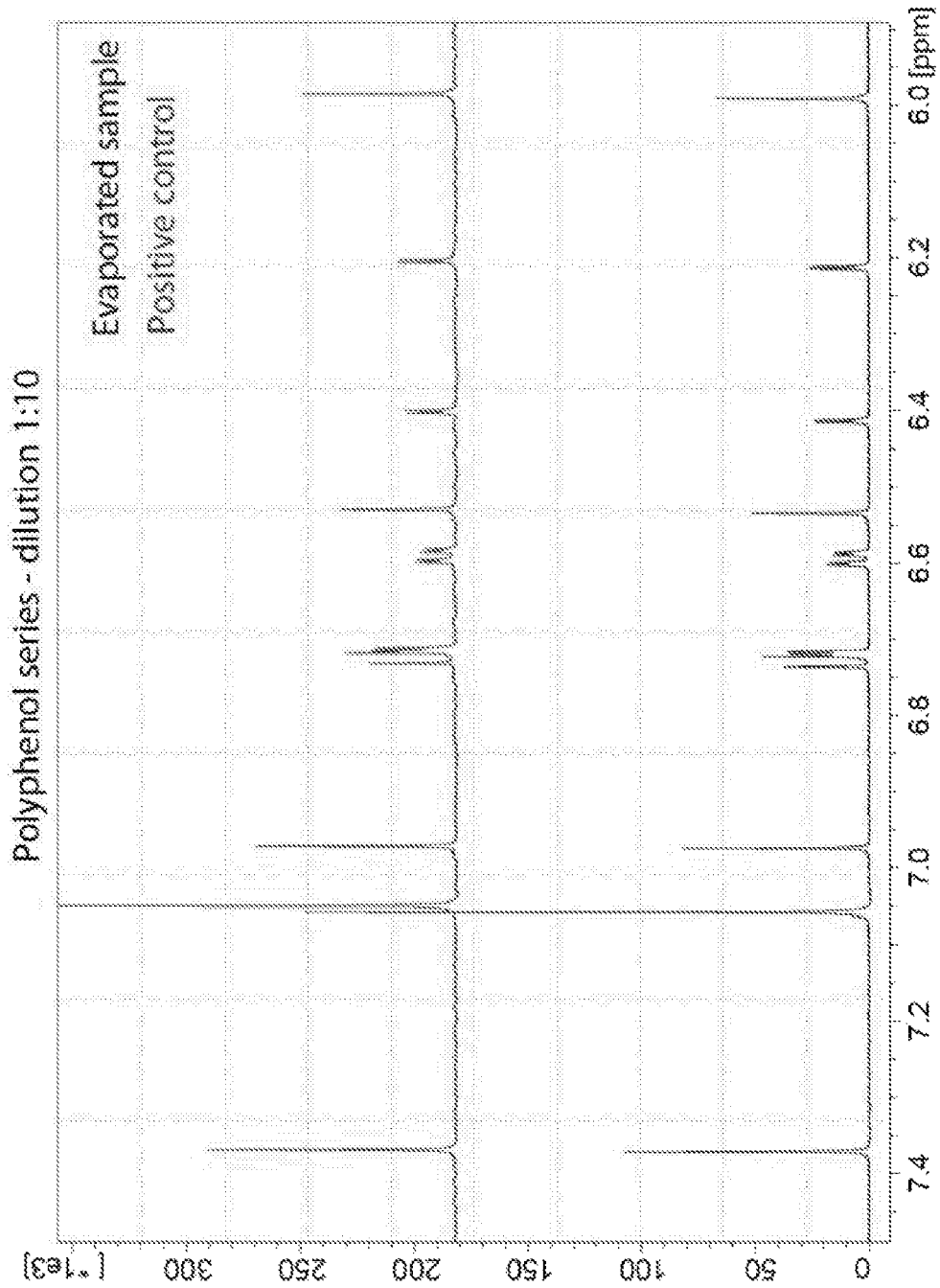
FIG. 8 shows the NMR spectrum of a mixture of polyphenols.

FIG. 8 shows the NMR spectrum of an academic mixture of polyphenols, comprising EGCG, 5-(3,4-dihydroxyphenyl)-γ-valerolactone, myricetin and gallic acid.

A slight peak shift can be observed for gallic acid, which may be due to a shift in pH. Further there seem to be no significant differences between the evaporated sample and the positive control, which indicates that the temperature sensitive ECGC has been maintained integrally. Moreover, thermo-sensitive compounds such as ECGC, 5-(3,4-dihydroxyphenyl)-γ-valerolactone, and myricetin appears not to be affected by the evaporation step. Furthermore, no scaling effects were observed in the analyte concentration, which illustrates the usefulness of the present process and device for solvent exchange for an NMR spectrum.

Figure 9:
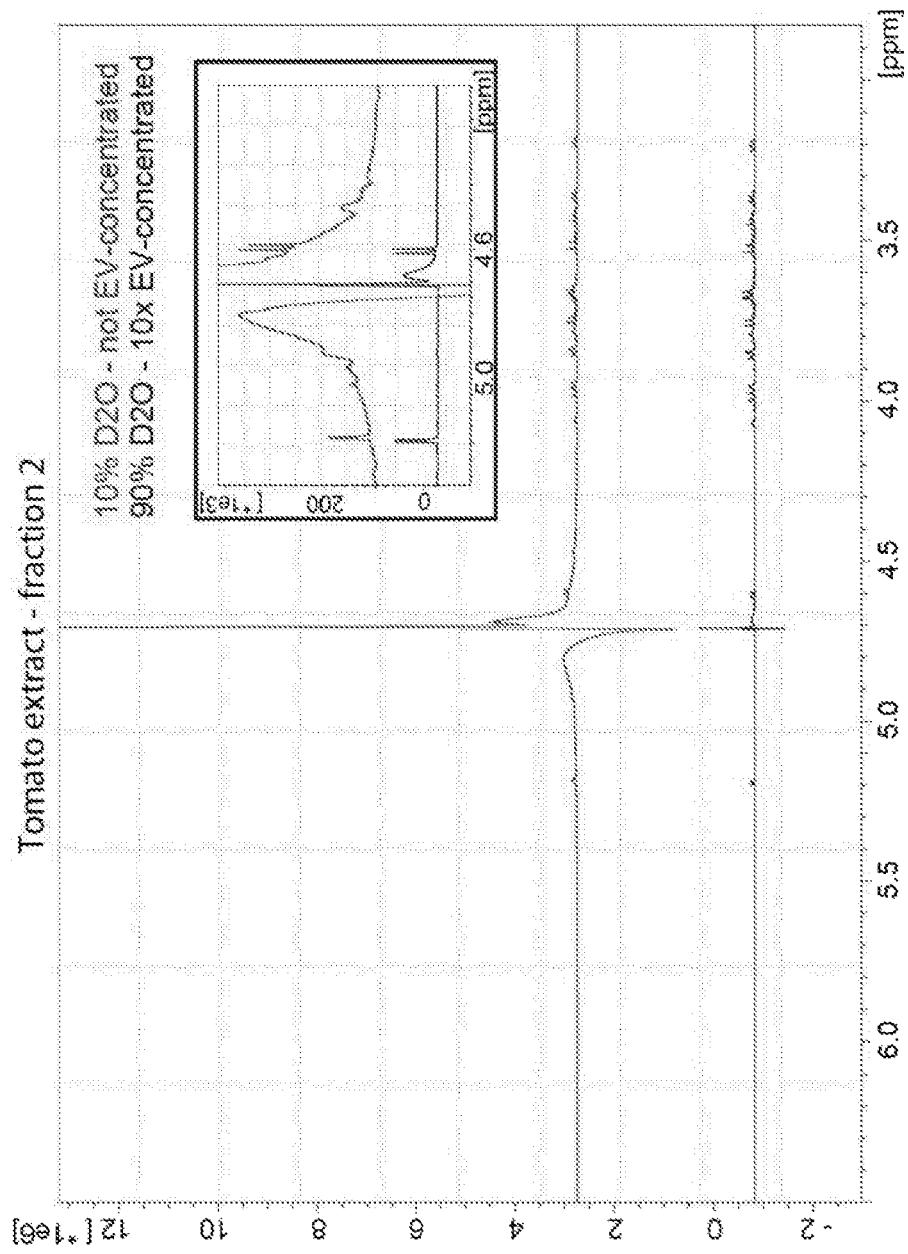
FIG. 9 shows a comparison of diluted fractionated tomato extract, wherein the top sample was not evaporated and contained 225 μL of a ten times diluted fractionated tomato extract, while the bottom sample shows the evaporated sample which was concentrated 10 times by evaporation and subsequently diluted in 225 μL $D_2O$.

FIG. 9 shows a comparison between a non-evaporated (top) and an evaporated (bottom) fractionated tomato sample. The top sample was not evaporated and contained 225 µL of a ten times diluted fractionated tomato extract (sugars mainly). The bottom sample shows the evaporated sample which was concentrated 10 times by evaporation and subsequently diluted in 225 µL $D_2O$. The non-evaporated sample contained 10% $D_2O$ and roughly the same concentration analyte as the evaporated sample.

Evaporation was used to replace 90% water with $D_2O$. Not surprisingly, the non-evaporated sample shows much larger artifacts due to the abundant presence of water than is the case for the evaporated sample. The peaks for β-glucose cannot be quantified for the non-evaporated sample, while this is still possible for the evaporated sample, indicating the particular usefulness for the present method and device for the analysis of complex and unknown samples.

Figure 10:
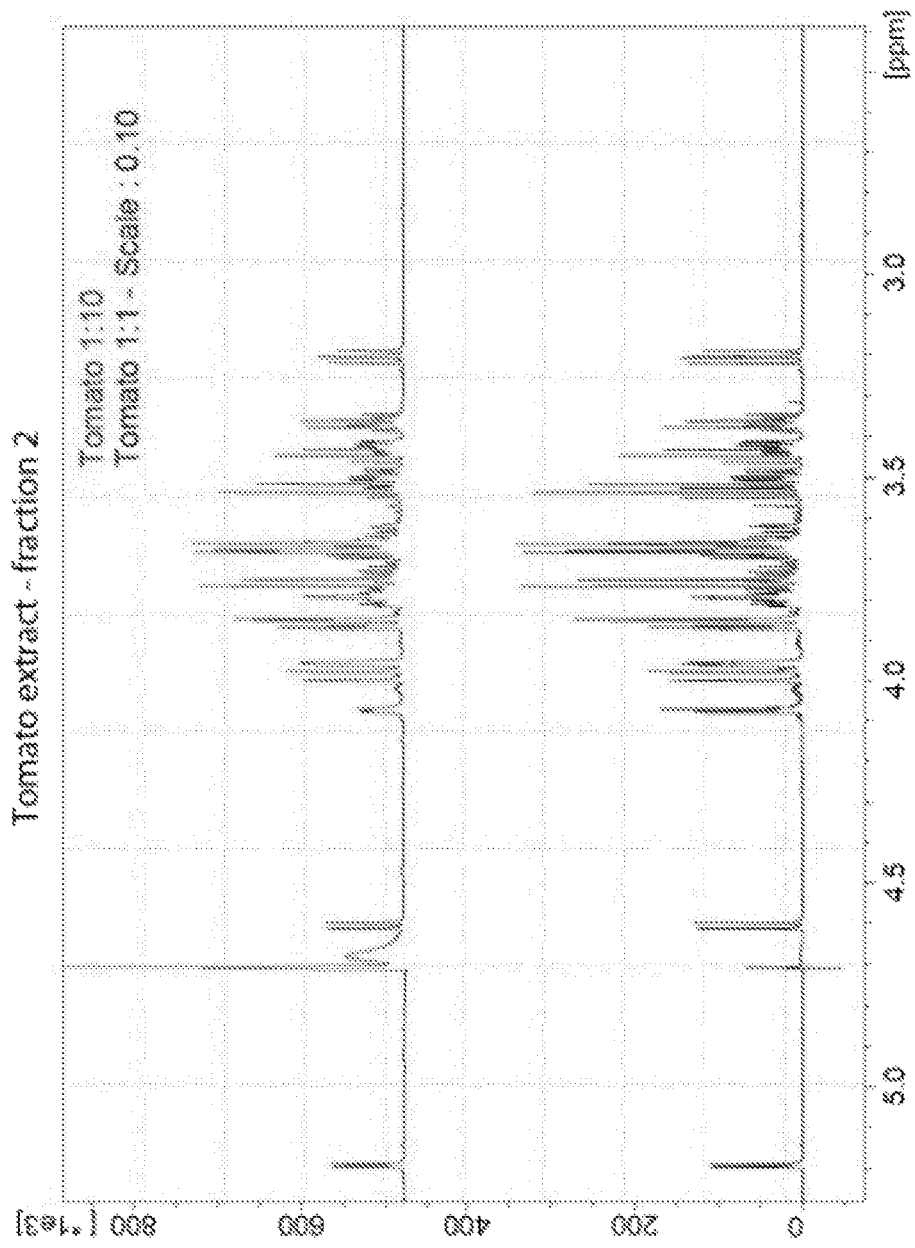
FIG. 10 illustrates the effect of analyte concentration on detectability for fractionated tomato extract at a 1:10 and 1:1 concentration.
Figure 11:
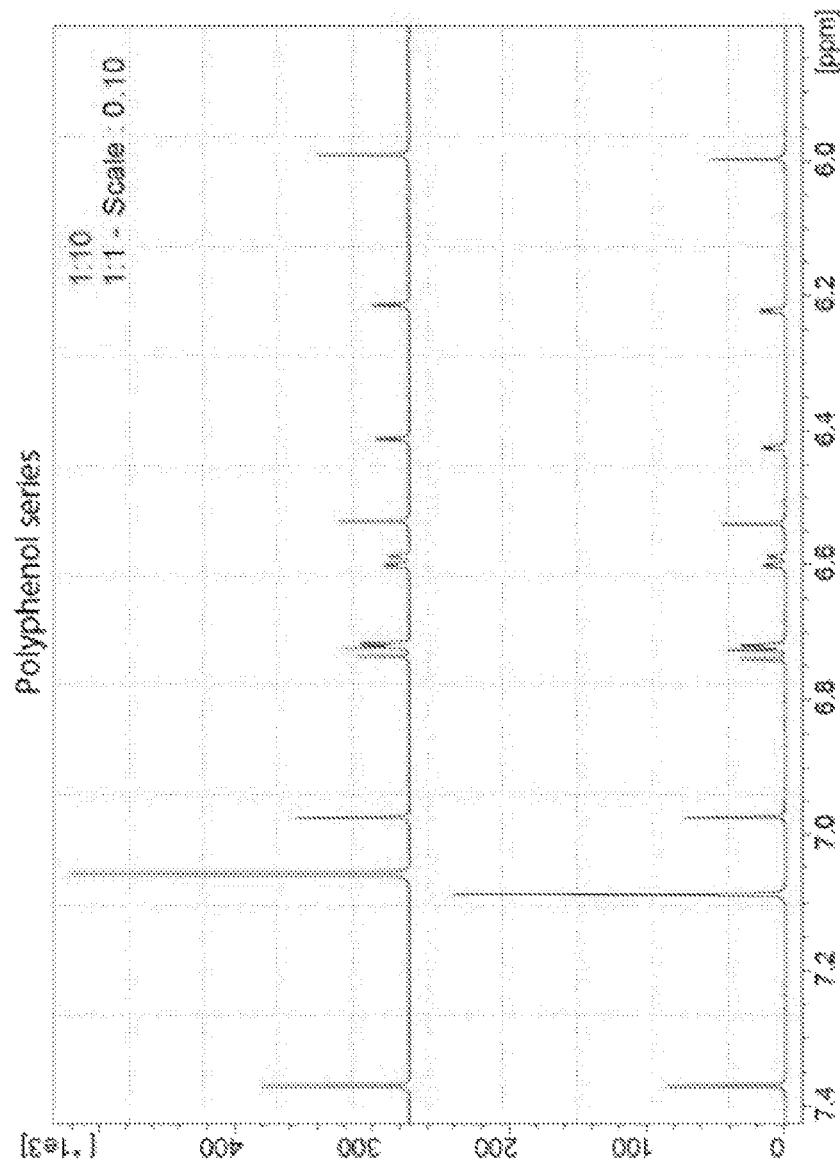
FIG. 11 illustrates the effect of analyte concentration on detectability for a polyphenol mixture at a 1:10 and 1:1 concentration.

FIGS. 10 and 11 depict the effects of analyte concentration on detectability. FIG. 10 shows a fractionated tomato extract at a 1:10 and 1:1 concentration; FIG. 11 shows a polyphenol mixture at a 1:10 and 1:1 concentration. The 1:1 concentrations have been downscaled by a factor 10 in order to enable comparison. The buffer for the polyphenol sample was methanol, for the tomato sample water and for the carrot extract a mixture of these two. From the above qualitative results, it can be concluded that the difference in vapour pressure of these two buffers does not significantly influence the evaporation efficiency.

The top sample in FIG. 10 shows a fractionated tomato extract (sugars) that was ten times diluted in water, ten times concentrated by evaporation and ten times diluted in D-water. The bottom sample has been treated likewise, except that the first dilution step has not taken place. Furthermore, the scale for the bottom sample has been reduced ten times to enable visual comparison between the two samples. For the case of the tomato, the result shows a slight non-linearity in scaling leading to a higher signal for the concentrated sample.

Furthermore the peak for fructose is more reduced with respect to the other peaks. Two peaks, marked x1 and x2, disappear completely. The difference might be due to adsorption effects or measurement artifacts.

The fact that the positive control (in FIG. 4) gives the same result as the evaporated sample, proves that the evaporation step is not responsible for this.

FIG. 11 shows the same procedure for the polyphenol series in methanol. Here the scaling is perfectly linear. Again a peak shift can be observed for gallic acid, probably due to a difference in pH between the two samples.

SUMMARY OF THE RESULTS

Fractionated tomato, whole carrot and an academic sample of polyphenols showed no significant degeneration or removal of compounds during the solvent replacement process. The arrangement and method further performed both for volatile and less volatile running buffers; while it appears that even volatile components such as acetic acid remain in solution during the evaporation process. Yet further, thermo-sensitive components such as EGCG were not affected by the evaporation step.

The invention claimed is:

1. A device for selective solvent evaporation from a liquid feed, the feed comprising one or more components diluted in at least a first solvent or a solvent blend, comprising:
   a) a first tubular vessel having a distal end or a channel suitable for the formation of a droplet of a first volume, at a rate of inflow rate $r_1$, at the tip or in the lumen of the tubular vessel, and
   b) means for subjecting the droplet to a solvent removal step at a solvent removal rate $r_2$ to evaporate at least part of the first solvent or solvent blend, to accumulate the components in the feed in the droplet during the evaporation process at a rate of accumulation $r_3$, to obtain a concentrated feed volume in a concentrated droplet, wherein the evaporation and/or inflow rates are continuously adjusted to achieve a desired accumulation rate, and
   means (c) to transfer the concentrated sample droplet into a second fluid to allow change of solvent composition and/or dilution and/or to allow transfer to another analysis method;
   wherein at least one of $r_1$, $r_2$ or $r_3$ are controlled by an automated system comprising a machine vision unit that sequentially acquires one or more images of the droplet, processes the acquired images to determine one or more droplet parameters; and communicates the parameters to a comparison means.

2. The device according to claim 1, further comprising a means to determine at least two selected from the group consisting of $r_1$, $r_2$ and $r_3$.

3. The device according to claim 1, wherein the device comprises at least one selected from the group consisting of; a means to adjust pressure, a means to adjust temperature and a means to adjust gas flow rate at the gas/liquid interface of the droplet.

4. The device according to claim 1, wherein the automated system comprises at least one sensor, or at least one actuator or at least one sensor and at least one actuator.

5. The device according to claim 4, wherein the comparison means correlates sensor data to a set point value, and delivers an adjustment signal to an actuator to adjust the magnitude of the parameter controlled by the actuator, wherein the actuator controls evaporation rate $r_2$.

6. The device according to claim 1, further comprising a means for dispensing the droplet from the distal end or within the capillary means.

7. The device according to claim 1, further comprising a means to maintain the keeper solvent in a liquid phase during step b).

8. The device according to claim 7, further comprising a means to add the keeper solvent to the first solvent or solvent blends, or to a sample droplet prior to, or during the evaporation process, or to both the first solvent or solvent blends and to a sample droplet prior to, or during the evaporation process.

9. An arrangement for the multi-dimensional separation of a liquid feed comprising one or more components, comprising:
   i) at least a first separation device for the separation of compounds in the sample diluted in a first solvent or solvent blend in a first dimension into a first liquid feed comprising one or more components; and
   ii) a device according to claim 1, for selective solvent evaporation from the first liquid feed to obtain one or more concentrated droplets, and optionally
   iii) at least a second separation device for the separation of the components in the concentrated sample droplets in a second dimension; and optionally
   iv) a device for analyzing the components in the concentrated droplets.

10. The arrangement according to claim 9, wherein the device for analyzing the compounds in the concentrated droplets comprises a physical, biochemical and/or chemical analysis tool.

11. The arrangement of claim 9, further comprising a means to add a keeper solvent to the first solvent or solvent blends, and/or to a sample droplet prior to or during the evaporation process.

12. A process for the selective solvent removal from a liquid feed comprising one or more components diluted in at least a first solvent or a solvent blend, comprising the steps of:
   a) forming an amount of the feed derived from a first separation device into a droplet with a first defined volume at the distal end or within a tubular vessel at a defined rate of inflow $r_1$ at the tip of the capillary or in the channel, and
   b) subjecting the droplet to a solvent removal step to remove at least part of the solvent or solvent blend at a defined rate of solvent removal $r_2$ to remove at least part of the first solvent or solvent blend, and accumulation of components in the sample in the droplet during the solvent removal process at a rate of the accumulation $r_3$, to obtain a concentrated feed droplet, wherein rates $r_1$ and $r_2$ depend on the rate of accumulation $r_3$, and c) rediluting the concentrated droplet in a second solvent or solvent blend;

wherein the defined droplet surface area is monitored by machine vision.

13. The process according to claim 12, wherein the droplet has a defined volume with a first defined surface area.

14. The process according to claim 12, wherein the loss of solvent through evaporation is equal or higher to the amount of fluid sample added to the droplet through the capillary vessel.

15. The process according to claim 12, wherein the defined droplet volume is kept constant.

16. The process according to claim 12, wherein the concentrated droplet or a re-dissolved or re-diluted sample droplet is dispensed from the tubular vessel.

17. The process according to claim 12, further subjecting the re-dissolved or re-diluted sample to a second separation process.

18. A process for the selective solvent removal from a liquid feed comprising one or more components diluted in at least a first solvent or a solvent blend, comprising the steps of:

a) forming an amount of the feed derived from a first separation device into a droplet with a first defined volume at the distal end or within a tubular vessel at a defined rate of inflow $r_1$ at the tip of the capillary or in the channel, and b) subjecting the droplet to a solvent removal step to remove at least part of the solvent or solvent blend at a defined rate of solvent removal $r_2$ to remove at least part of the first solvent or solvent blend, and accumulation of components in the sample in the droplet during the solvent removal process at a rate of the accumulation $r_3$, to obtain a concentrated feed droplet, wherein the droplet comprises a keeper solvent;

wherein the keeper solvent is a solvent or solvent blend that will essentially not evaporate during the process step b), and wherein the keeper solvent is at least present in an amount sufficient to retain the components in the analyte samples in a liquid state, either dissolved, dispersed and/or suspended; during and after the evaporation process, thereby preventing the sample concentration process from going to dryness.

19. The process according to claim 18, wherein the keeper solvent comprises one or more normally solid compounds, one or more normally liquid compounds, and/or one or more normally gaseous compounds, which are liquid under the process conditions.

20. The process according to claim 19, wherein the normally liquid solvent is selected from carbonaceous compounds of low normal volatility, including ethylene glycol, glycerol, propylene glycol, DMF, DMSO, 1-hexanol, 1-octanol, hydrocarbons, preferably n-alkanes, more preferably octane, decane or tetradecane, waxes; silicone waxes and/or silicone oils.

21. The process according to claim 18, wherein the keeper solvent comprises carbon dioxide under supercritical conditions.

22. The process according to claim 18, wherein the keeper solvent is a deuterated species.

23. The process according to claim 18, wherein the keeper solvent is present in the solvent or solvent blend prior to the formation of the droplet, and/or wherein it is added during the formation of the droplet.

* * * * *